(12) United States Patent
Huang

(10) Patent No.: US 12,330,149 B2
(45) Date of Patent: Jun. 17, 2025

(54) MOBILE BIOREACTOR SERVICE SYSTEM

(71) Applicant: Ark Biotech Inc., Westwood, MA (US)

(72) Inventor: Zheng Huang, Bolton, MA (US)

(73) Assignee: Ark Biotech Inc., Westwood, MA (US)

( * ) Notice: Subject to any disclaimer, the term of this patent is extended or adjusted under 35 U.S.C. 154(b) by 0 days.

(21) Appl. No.: 18/830,226

(22) Filed: Sep. 10, 2024

(65) Prior Publication Data

US 2025/0108383 A1 Apr. 3, 2025

Related U.S. Application Data

(60) Provisional application No. 63/587,507, filed on Oct. 3, 2023.

(51) Int. Cl.
*C12M 1/00* (2006.01)
*B01J 19/00* (2006.01)

(52) U.S. Cl.
CPC ....... *B01L 13/02* (2019.08); *B01L 2300/0681* (2013.01)

(58) Field of Classification Search
CPC .................. B01L 13/02; B01L 2300/0681
See application file for complete search history.

(56) References Cited

U.S. PATENT DOCUMENTS

| | | |
|---|---|---|
| 2010/0266448 A1 | 10/2010 | Regits |
| 2018/0030398 A1* | 2/2018 | Castillo ................. C12M 41/40 |
| 2021/0371781 A1* | 12/2021 | Farmer ................. C12M 41/16 |
| 2022/0056394 A1* | 2/2022 | Leung ..................... A23L 13/00 |
| 2022/0143610 A1 | 5/2022 | Biz |
| 2023/0220324 A1 | 7/2023 | Heinrichs |
| 2023/0288933 A1 | 9/2023 | Maggiore |
| 2023/0357702 A1* | 11/2023 | Frigård .................. C12M 23/40 |

\* cited by examiner

*Primary Examiner* — Jill A Warden
*Assistant Examiner* — Alex Ramirez
(74) *Attorney, Agent, or Firm* — Van Pelt, Yi & James LLP

(57) ABSTRACT

A mobile bioreactor service system includes a control interface, a physical interface, and a service system. The control interface connects to one or more valves. The physical interface connects one or more tubes to a bioreactor enabling process fluids to be physically transferred to/from the bioreactor based on a corresponding state of the one or more valves. The service system performs a service on the bioreactor.

27 Claims, 17 Drawing Sheets

MOBILE BIOREACTOR SERVICE SYSTEM

CROSS REFERENCE TO OTHER APPLICATIONS

This application claims priority to U.S. Provisional Patent Application No. 63/587,507 entitled MOBILE BIOREACTOR SERVICE SYSTEM filed Oct. 3, 2023 which is incorporated herein by reference for all purposes.

BACKGROUND OF THE INVENTION

A cell culture production plant may be comprised of a plurality of bioreactors. In a conventional cell culture production plant, as seen in FIG. 1, each bioreactor has a vessel and a skid. Cells grow in the vessel, while the skid provides essential functional support. During live cell culture, a big part (the most expensive part) of the skid is idle and under-utilized. For example, a clean-in-place (CIP) system is not used while cells are being cultivated within the bioreactor.

In a conventional cell culture production plant (common in biopharma industry), bioreactors are connected to feed/harvest vessels and to each other by a complex network of fixed piping and valves as seen in FIG. 2B. These vessels are supported by fixed utility networks (e.g., gas, water, steam, CIP/SIP circuits). FIG. 2A is an example of a fixed CIP system. The complexity of bioreactor systems and factory layout make it expensive to build, commission, operate, and troubleshoot.

The inter-dependence of the fixed utility networks makes the system susceptible to disruption, delay, and a single point of failure. If there is a failure with one of the fixed utilities, then all of the bioreactors at the cell culture production plant may be affected. For example, if there is a problem with the CIP system, then none of the bioreactors connected to the particular CIP system can be cleaned. If one of the valves doesn't close properly, then it is possible for a first bioreactor to contaminate a second bioreactor. Troubleshooting the single point of failure may require taking all of the bioreactors offline. It is often difficult to schedule routing operations, debottleneck, and recover from any disruptions. This leads to significantly lower real-world productivity and throughput than the theoretical maximum.

Due to the cost-sensitive nature of the emerging cellular agriculture industry, the current cell culture production systems designed for biopharma are prohibitively expensive. A more suitable approach for large-scale cell culture production is needed.

BRIEF DESCRIPTION OF THE DRAWINGS

Various embodiments of the invention are disclosed in the following detailed description and the accompanying drawings.

DETAILED DESCRIPTION

Figure 1:
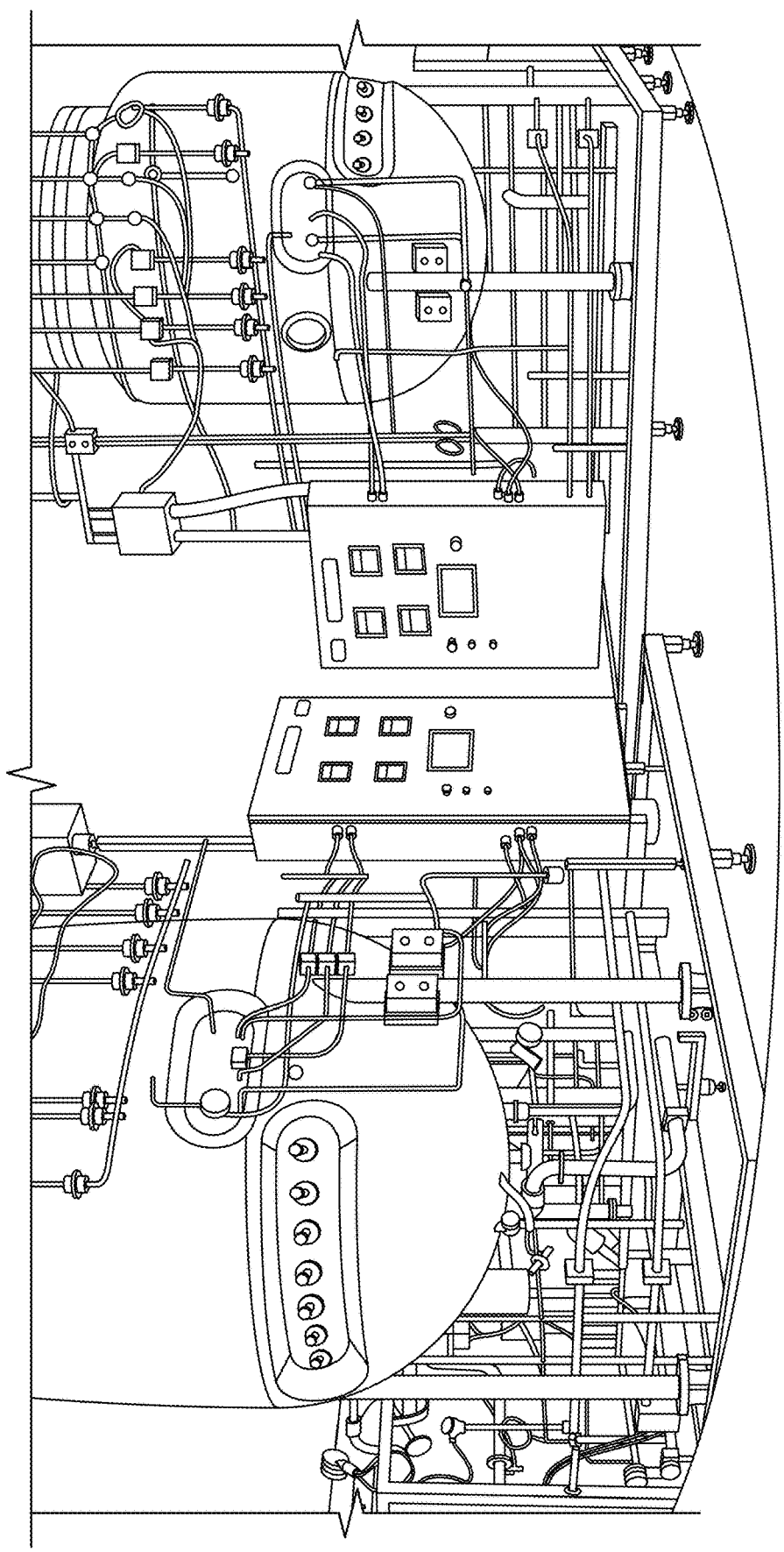
FIG. 1 illustrates an example of a bioreactor having a vessel and a skid.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A mobile bioreactor service system is disclosed. The mobile reactor service system removes the single point of failure associated with conventional cell culture production plants. For example, if a mobile bioreactor service system is connected to a bioreactor to perform a CIP operation and there is a problem with the mobile bioreactor service system, the mobile bioreactor service system can be taken offline and repaired, in the meantime, a backup mobile reactor service system can be put in service immediately without halting the production. The operation of one or more other bioreactors in the cell culture production plant is unaffected. Compared to fixed utility networks associated with conventional cell culture production plants, the disruption (e.g., time and resources) caused by taking the mobile bioreactor service system offline is minimal. As a result, the mobile bioreactor service system will greatly lower capital investment for cell culture production plants and improve the robustness of operation.

The mobile bioreactor service system includes a plurality of wheels. In some embodiments, the mobile bioreactor service system is configured to travel in any direction in a 2-dimensional plane. In some embodiments, the mobile bioreactor service system is remotely controlled by a user via an input device (e.g., keyboard, joystick, controller, etc.) to travel and service the different bioreactors in the cell culture production plant. The mobile bioreactor service system may be remotely controlled via a wired or wireless connection (e.g., Wi-Fi, Bluetooth, Zigbee, Z-wave, etc.). In some embodiments, the mobile bioreactor service system autonomously travels and services the different bioreactors in the cell culture production plant. The mobile bioreactor service system may be programmed to service the different bioreactors in a particular order to maximize the throughput of the different bioreactors. In some embodiments, the mobile bioreactor service system is manually moved around (e.g., a cart) from the different bioreactors in the cell culture production plant. In some embodiments, the mobile bioreactor service system is configured to travel along a set of rails (e.g., tracks).

In some embodiments, the mobile bioreactor service system is a mobile solution prep skid. Conventional solution prep vessels are stationary because they are large and heavy. For example, a 10,000 liter vessel bioreactor needs at least a 10,000 liter media prep tank. Media ingredients are added to the media prep tank that includes water until the solution is diluted to a desired concentration. The media having the desired concentration is subsequently transferred from the solution prep vessel to the bioreactor. In contrast, the mobile solution prep skid includes a compact prep vessel (e.g., 2000L media prep tank for a 10,000L vessel bioreactor) that may be transported on the plurality of wheels to a plurality of different bioreactors. The compact prep vessel is partially filled with water, media ingredients (powder or concentrate) is then added. Additional water is added to the compact prep vessel to dissolve the media ingredients. The partially dissolved solution concentrate is recirculated from the compact prep vessel to a filter (e.g., tangential flow filter) and provided to the bioreactor via the filter. Water is continually added to the compact prep vessel to keep the solution concentrate at a particular volume. Over time, the media in the bioreactor is diluted to the desired concentration, while the compact prep vessel mainly stores water with trace amounts of the solution concentrate.

In some embodiments, the mobile bioreactor service system is a mobile CIP skid. In some embodiments, the mobile bioreactor service system is a mobile SIP skid.

The mobile bioreactor service system is configured to connect to a plurality of bioreactors via a physical interface. The physical interface connects one or more tubes associated with the mobile bioreactor service system to the bioreactor, enabling process fluids to be physically transferred to/from the bioreactor. The process fluids may include water, a base, an acid, detergent, steam, chlorine dioxide, air, media, feed, an inoculant, etc.

In conventional cell culture production plants, an aseptic connection is sterilized using a steam-in-place method, a process that can take over an hour to establish a sterile connection and an additional half-hour to disconnect a sterile connection. Although single-use connectors and disconnectors offer faster sterile connections, they are costly and have size limitations. The physical interface includes a sterile connector system that enables quick connection/disconnection between a bioreactor and the mobile bioreactor service system. The sterile connector system enables the rapid turnaround of bioreactors because it sterilizes the bioreactor using chemical gases, such as chlorine dioxide. The amount of time associated with establishing a sterile connection and disconnecting the sterile connection can be reduced from 1.5 hours to around 15 minutes.

Figure 3A:
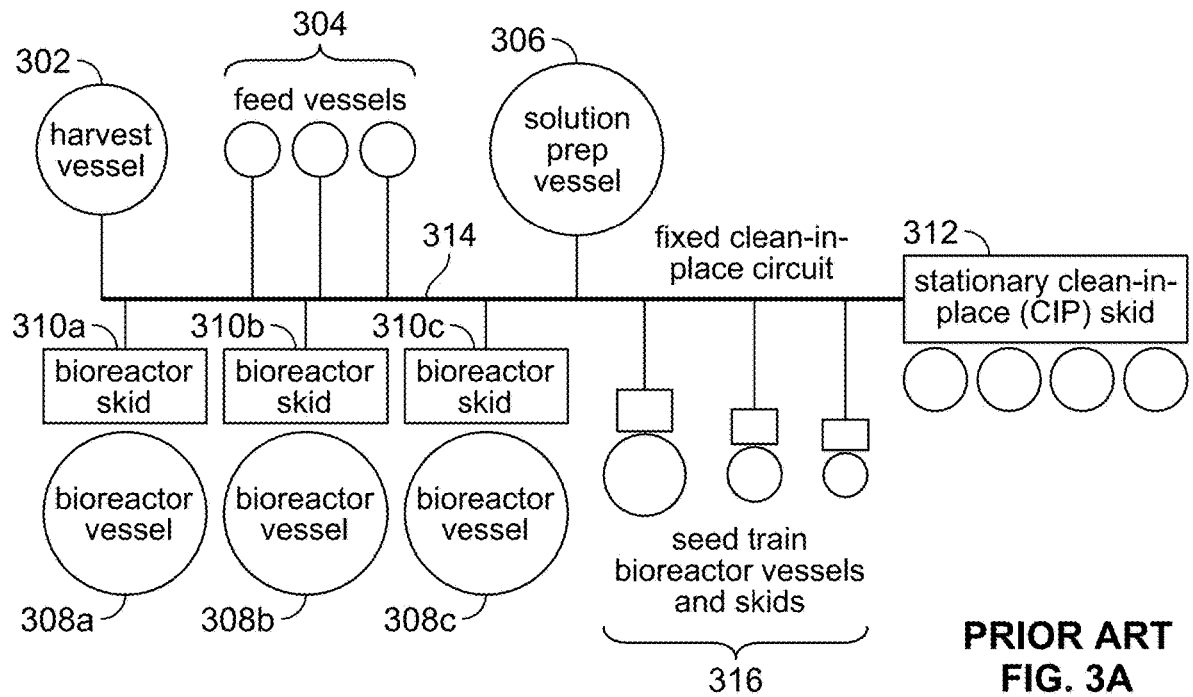
FIG. 3A illustrates a block diagram of a cell culture facility with a fixed clean-in-place circuit.

FIG. 3A is a block diagram illustrating a cell culture facility with a fixed clean-in place circuit. As seen in FIG. 3A, the cell culture facility includes a harvest vessel 302, feed vessels 304, a solution prep vessel 306, bioreactor vessels 308a, 308b, 308c and corresponding bioreactor skids 310a, 310b, 310c, and seed train bioreactor vessels and skids 316 being connected to stationary clean-in-place skid 312 via a fixed clean-in-place circuit 314. A problem with stationary clean-in-place skid 312 or fixed clean-in-place circuit 314 affects the operation of harvest vessel 302, feed vessels 304, a solution prep vessel 306, bioreactor vessels 308a, 308b, 308c and corresponding bioreactor skids 310a, 310b, 310c, and seed train bioreactor vessels and skids 316. Due to the complexity of the fixed piping network, it is difficult to schedule and debottleneck operations. Troubleshooting and determining the source of the problem is difficult and time-consuming.

Figure 3B:
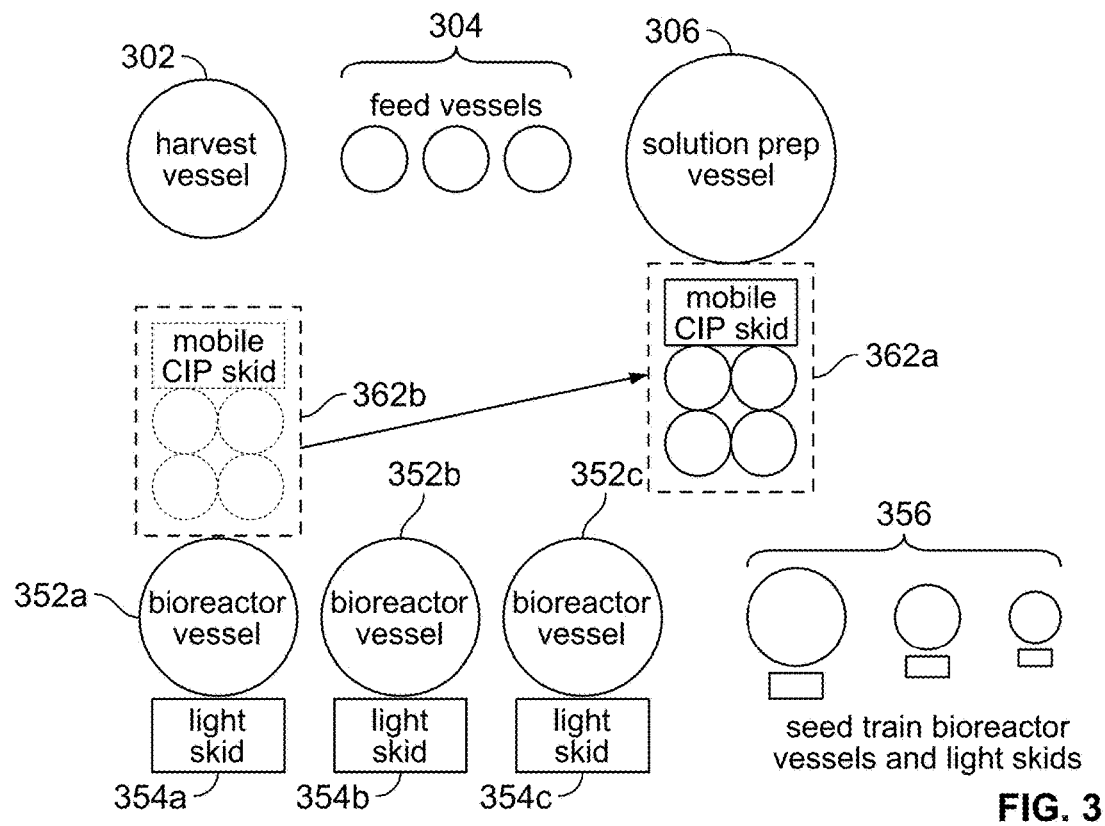
FIG. 3B illustrates a block diagram of a cell culture facility with a mobile bioreactor service system in accordance with some embodiments.

FIG. 3B is a block diagram illustrating a cell culture facility with a mobile bioreactor service system in accordance with some embodiments. In the example shown, stationary CIP skid 312 and fixed clean-in-place circuit 314 have been replaced with a mobile CIP skid that may move between a first position 362a and a second position 362b. Although FIG. 3B depicts the mobile CIP skid moving between two positions, the mobile CIP skid may move between n positions. Although FIG. 3B depicts the cell culture facility having one mobile CIP skid, the cell culture facility may have n mobile CIP skids.

A first mobile CIP skid may become defective. Instead of taking the entire cell culture facility offline to troubleshoot the problem associated with the CIP skid, the first mobile CIP skid may replaced with a second mobile CIP skid. When compared with the cell culture facility of FIG. 3A, the amount of time and resources needed to troubleshoot the problem associated with the cell culture facility of FIG. 3B is reduced. Although FIG. 3B depicts the cell culture facility having three bioreactor vessels and three corresponding light skids, the cell culture may have m bioreactor vessels and p corresponding light skids.

Bioreactor vessels 308a, 308b, 308c have been slightly modified to become bioreactor vessels 352a, 352b, 352c, respectively. For example, bioreactor vessels 352a, 352b, 352c have been modified to include a port with an aseptic valve V4 that enables them to be connected to other bioreactors or feed/harvest vessels utilizing a sterile connector system, such as the sterile connector system depicted in FIG. 9.

Bioreactor skids 310a, 310b, 310c have been simplified to become bioreactor light skids 354a, 354b, 354c, respectively. Bioreactor light skids 354a, 354b, 354c include components needed to sustain live cell culture (i.e., gas flow controllers, sensors, filters, valves at aseptic boundary, and temperature control, etc.).

The remainder of the bioreactor skids 310a, 310b, 310c is only used to service bioreactor 308a, 308b, 308c, respectively, during batch turn-around and may be converted into mobile bioreactor service systems (mobile skids) that are shared among a number of bioreactors and auxiliary vessels. Each mobile bioreactor service system serves distinct functions, e.g., solution prep, clean in place, sterilization in place, harvest, etc. Depending on the size of the mobile bioreactor service system, these mobile utility systems may be on a cart, on wheels or on tracks. They may be brought to a vessel to service it and sent away after its job is done. FIG. 3B uses a mobile CIP skid, but other mobile skids may be used for other purposes.

Figure 4A:
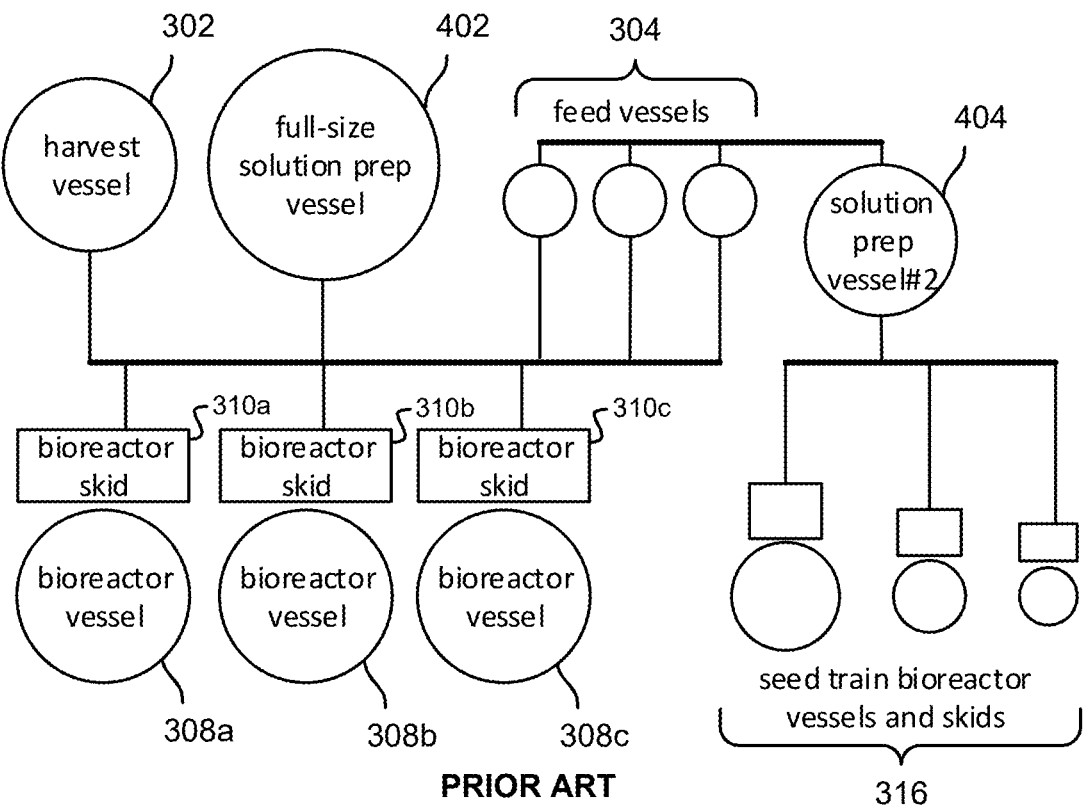
FIG. 4A is a block diagram illustrating a cell culture facility with fixed solution prep tanks.

FIG. 4A is a block diagram illustrating a cell culture facility with fixed solution prep tanks. In the example shown, the cell culture facility includes two fixed solution prep vessels 402, 404. Solution prep vessel 402 is configured to service bioreactor vessels 308a, 308b, 308c and solution prep vessel 404 is configured to service seed bioreactors 316 and feed vessels 304. Solution prep vessel 402 and solution prep vessel 404 are capable of servicing one bioreactor or one vessel at a time. If there is a problem with solution prep vessel 402 or solution prep vessel 404, then their corresponding bioreactors are offline until the problem is resolved.

Figure 4B:
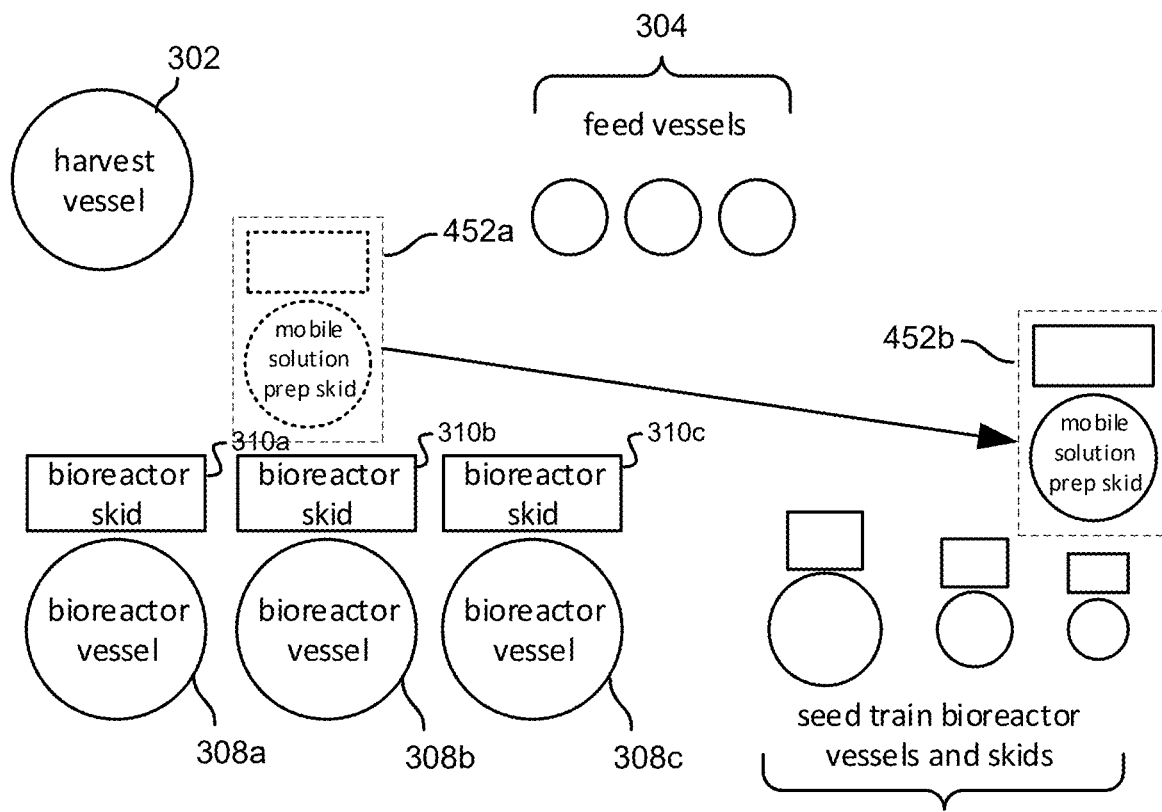
FIG. 4B is a block diagram illustrating a cell culture facility with a mobile solution prep skid in accordance with some embodiments.

FIG. 4B is a block diagram illustrating a cell culture facility with a mobile solution prep skid in accordance with some embodiments. In the example shown, the two fixed solution prep vessels 402, 404 and corresponding pipes have been replaced with a mobile solution prep skid. The mobile solution prep skid is capable of moving from bioreactor vessel to bioreactor vessel, or from location to location, such as location 452a and location 452b, to provide solution preparation services. Fixed piping for solution transfer is eliminated, which reduces cost and complexity associated with the cell culture facility. In contrast to the cell culture facility illustrated in FIG. 4A, if there is a problem with the mobile solution prep skid, a backup mobile solution prep skid may be used in its place while the mobile solution prep skid undergoes maintenance. This reduces the ability of the mobile solution prep skid to disrupt and delay operations in the cell culture facility.

Figure 5A:
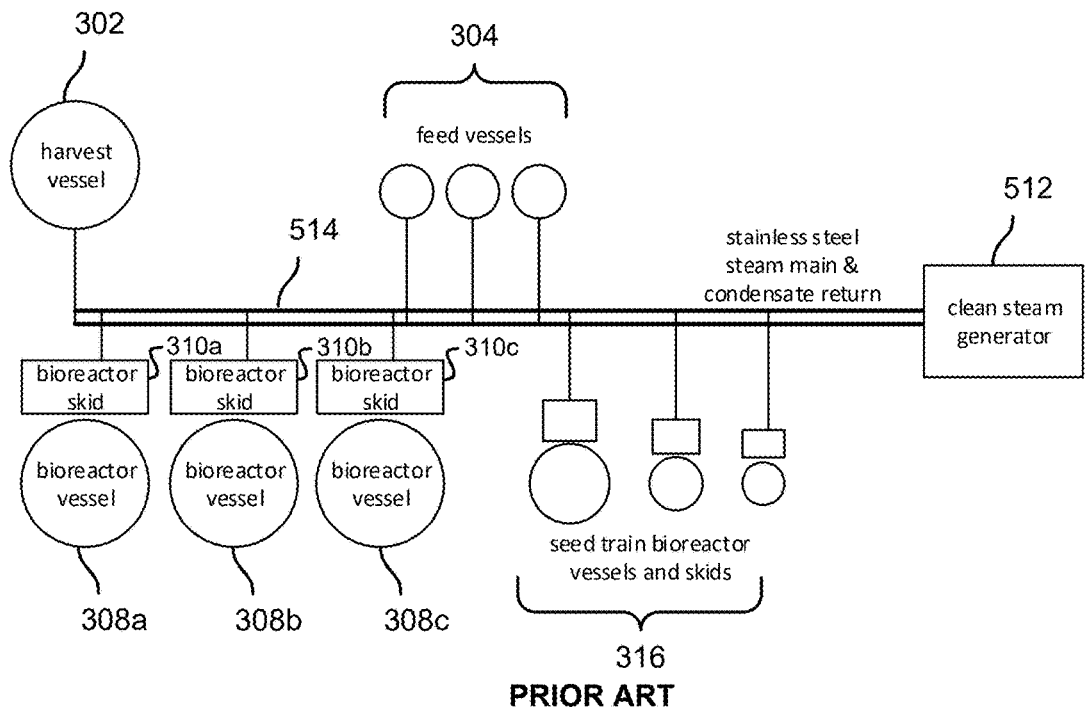
FIG. 5A is a block diagram illustrating a cell culture facility with a fixed steam-in-place system.

FIG. 5A is a block diagram illustrating a cell culture facility with a fixed steam-in-place system. In the example shown, the cell culture facility includes a clean steam generator 512 and a stainless steel steam main and condensate return 514. If there is a problem with clean steam generator 512, then none of the bioreactors 308a, 308b, 308c can undergo a SIP operation.

Figure 5B:
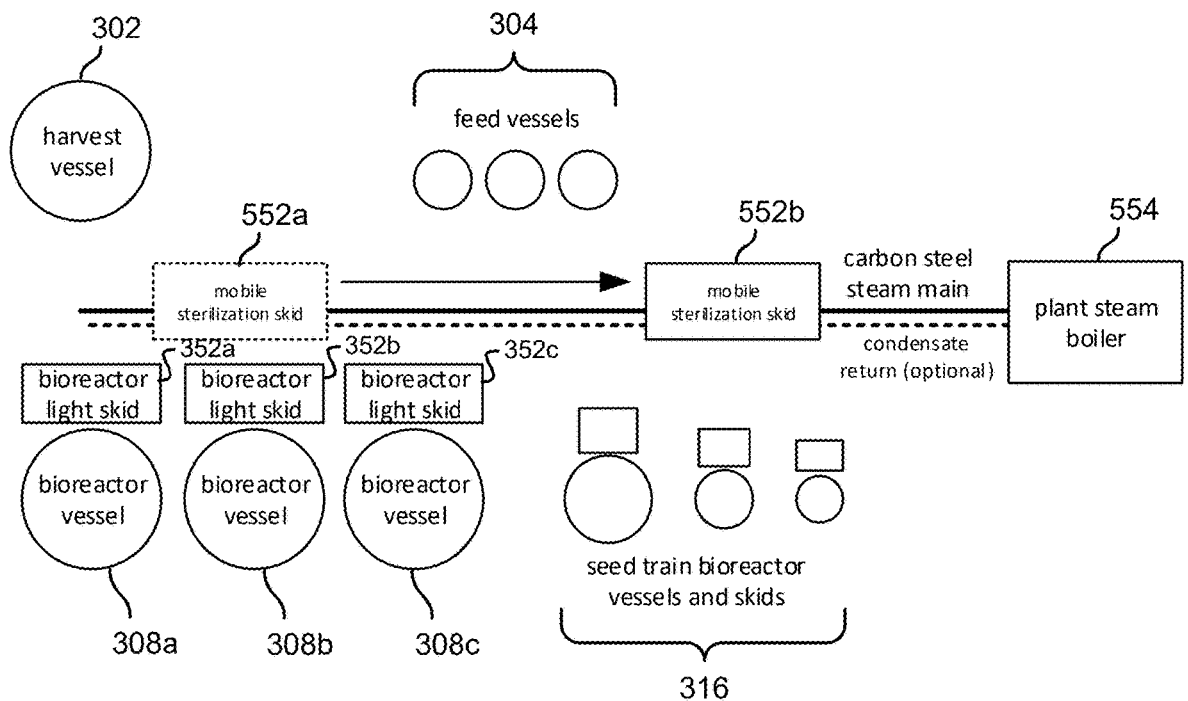
FIG. 5B illustrates a mobile steam-in-place skid in accordance with some embodiments.

FIG. 5B is a block diagram illustrating a cell culture facility with a mobile sterilization skid in accordance with some embodiments. In the example shown, the clean steam generator 512 and the stainless steel steam main and condensate return 514 have been replaced with a mobile sterilization skid, which greatly reduces cost and complexity. The mobile sterilization skid is capable of being moved to a plurality of locations, such as location 552a and location 552b. Also, the mobile sterilization skid can have a compact on-skid clean steam generator (FIG. 7) that uses plant steam boiler 554 as an energy source. The mobile sterilization skid can store a small amount of condensate (FIG. 7); therefore condensate return main line may not be necessary. With these changes, carbon steel plant steam boiler 554 and carbon steel steam main can replace expensive an all stainless steel clean steam system (the clean steam generator, the steam main, and the condensate return main, etc.), thus further reducing the cost of facility and operations.

In contrast to the cell culture facility illustrated in FIG. 5A, if there is a problem with the mobile sterilization skid, a backup mobile sterilization skid may be used in its place while the mobile sterilization skid undergoes maintenance. This reduces the ability of the mobile sterilization skid to disrupt and delay operations in the cell culture facility.

Utilizing a plurality of mobile bioreactor service systems instead of having dedicated fixed systems in place, a cell culture product plant can have much higher equipment utilization. Therefore, less capital investment (Table 1) is needed to reach the same production capacity. This alternative arrangement reduces the cost of the bioreactors, since the most expensive part of a bioreactor is the skid (70~80%), not the vessel (20~30%). The most complex/expensive (~60% of the cost) part of the skid (notably valves and piping to enable aseptic connections, CIP, and SIP) is not doing anything most of the time (>90% idle time).

The mobile bioreactor service systems include solution prep, clean-in-place, and sterilization skids. They move around to serve whichever reactors or media/harvest vessels that need a turn-around. For example, a plant of 12 bioreactors may need two, each of the shared skids (Table 1). It is desired to have one additional set of the shared skids as backup. Note that a plant of 36 bioreactors, one backup set is sufficient for redundancy instead of three backup sets (Table 2).

TABLE 1 compare capital investment for a conventional cell culture plant and a shared economy plant. Note that, the plant needs two of each mobile skid for normal operation. One additional set is for back up purpose.

|  | Conventional (12 × 20K) | | Shared Economy (12 × 20K) | |
| --- | --- | --- | --- | --- |
| Bioreactor vessel | 12 | $150,000 | 12 | $150,000 |
| Bioreactor skid | 12 | $650,000 | 12 | $150,000 |
| CIP circuit | 4 | $1,000,000 | | |
| Mobile CIP skid | | | 3 | $1,000,000 |
| Clean steam generator and piping | 2 | $2,000,000 | | |
| Mobile sterilization skid | | | 3 | $1,000,000 |
| Solution prep vessels + piping | 4 | $500,000 | | |
| Mobile solution prep skid | | | 3 | $750,000 |
| Commissioning | 1 | $6,000,000 | 1 | $3,000,000 |
| | | $25.6M | | $12.1M |

TABLE 2

Further cost reduction under shared economy for a larger plant. Note that, the plant needs six of each mobile skid for normal operation. One additional set is for back up purposes. Due to the mobile nature, fewer backup set (one set instead of three sets) is needed. Commissioning cost is also lower here given the mobile skid could be moved and commissioned in one place.

|  | Conventional (36 × 20K) | | Shared Economy (36 × 20K) | |
|---|---|---|---|---|
| Bioreactor vessel | 36 | $150,000 | 36 | $150,000 |
| Bioreactor skid | 36 | $650,000 | 36 | $150,000 |
| CIP circuit | 12 | $1,000,000 | | |
| Mobile CIP skid | | | 7 | $1,000,000 |
| Clean steam generator and piping | 6 | $2,000,000 | | |
| Mobile sterilization skid | | | 7 | $1,000,000 |
| Solution prep vessels + piping | 12 | $500,000 | | |
| Mobile solution prep skid | | | 7 | $500,000 |
| Commissioning | 1 | $18,000,000 | 1 | $6,000,000 |
| | | $76.8M | | $36.1M |

Mobile Solution Preparation Skid

Figure 6A:
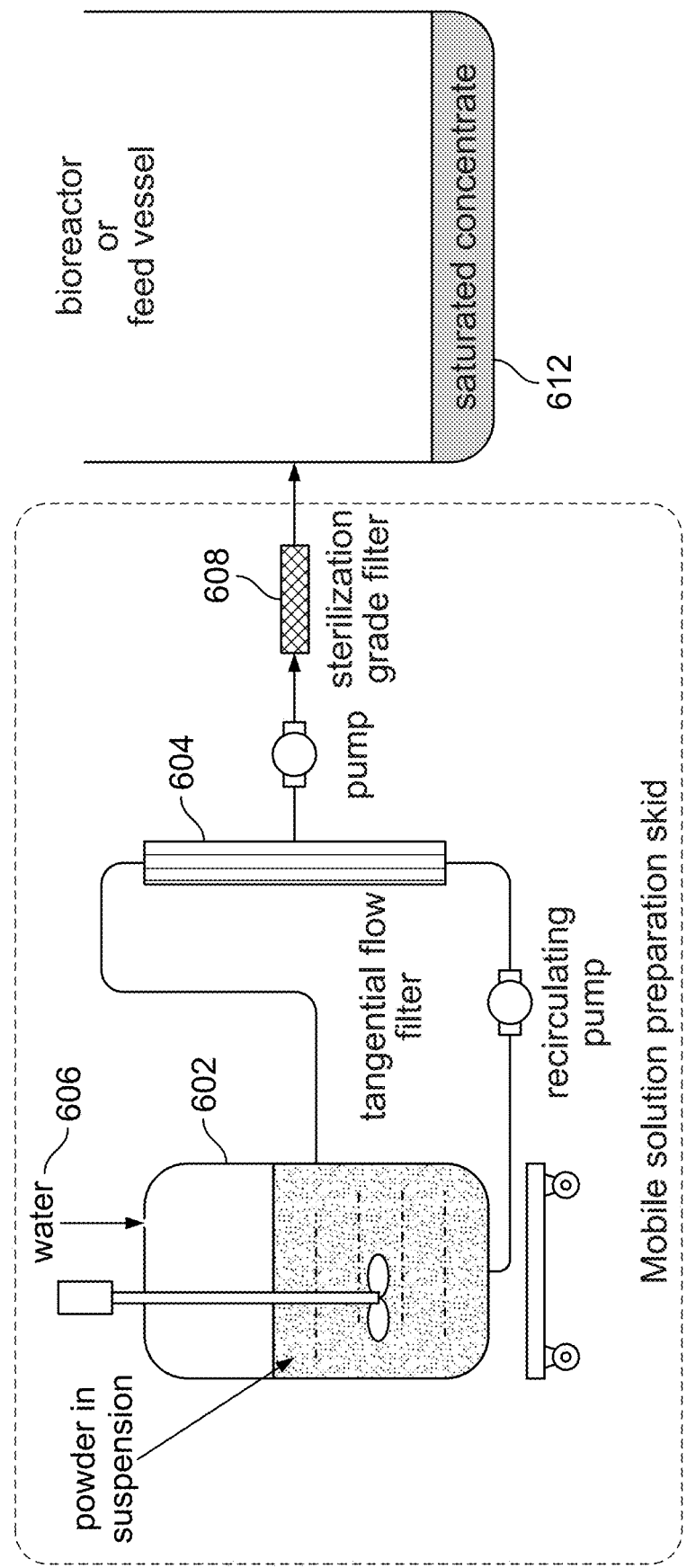
FIG. 6A illustrates a mobile solution preparation skid at the beginning of a media prep operation in accordance with some embodiments.
Figure 6B:
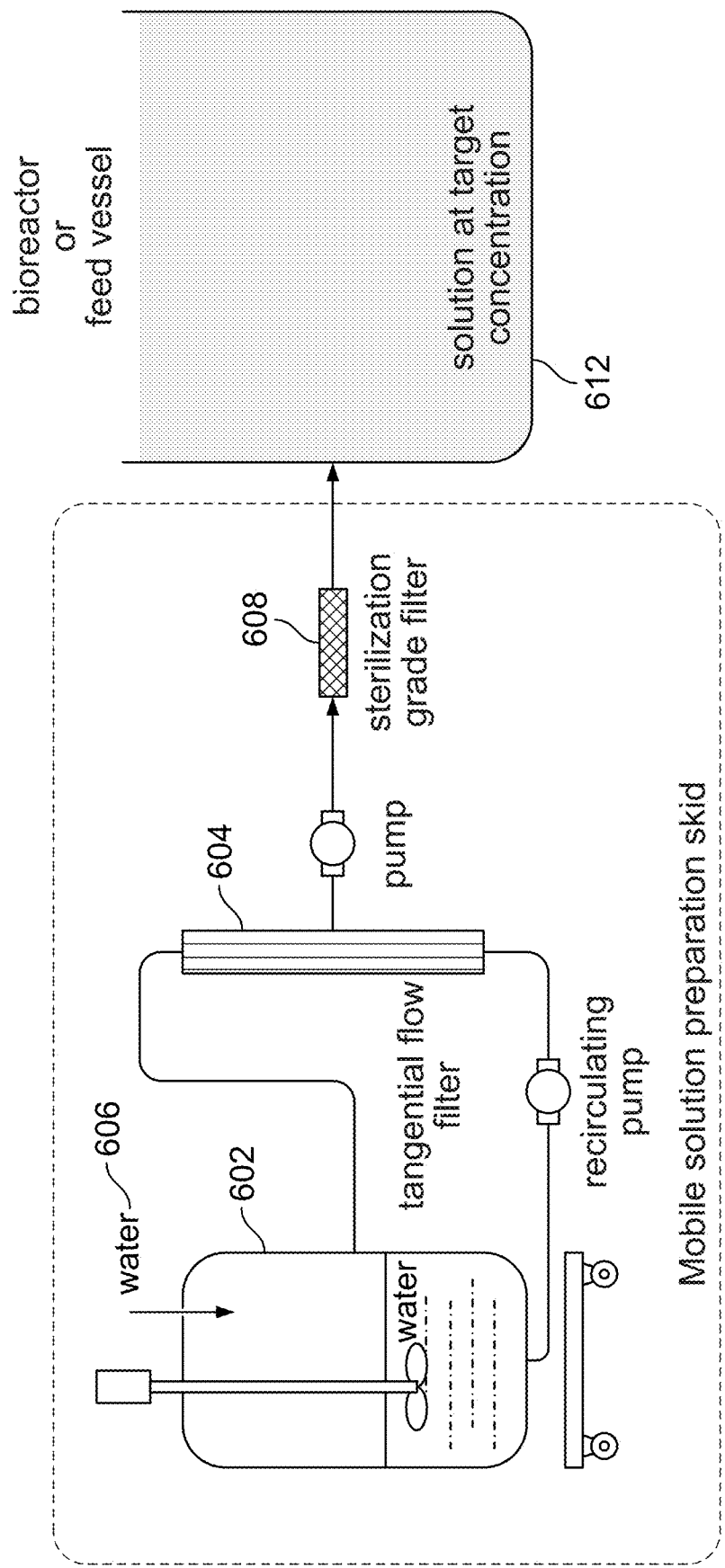
FIG. 6B illustrates a mobile solution preparation skid at the end of a media prep operation in accordance with some embodiments.

FIGS. 6A and 6B illustrate a mobile solution preparation skid in accordance with some embodiments. The mobile solution preparation skid makes solutions (i.e., cell culture media and feed solution) for a multitude of seed and production bioreactors. In a conventional cell culture production facility, the media preparation vessel is often among the biggest size for the vessels. In addition to mobile nature, the mobile solution preparation skid has a modest sized mixing tank, yet it is capable of preparing a large batch of solution that is much bigger than its own tank size. The solution preparation skid can self-clean and ready for the next vessel. Its filters could be re-useable after self-clean.

FIG. 6A illustrates an early phase of solution preparation. In the early phase, the powder is only partially dissolved, the suspension is recirculating between the mixing tank 602 and a tangential flow filter 604. In some embodiments, other types of filters are utilized (e.g., alternating tangential flow filter which uses compressed air and vacuum in place of the recirculating pump). Tangential flow filter 604 is configured to separate the dissolved solution concentrate from the mixture that contains undissolved powder. Dissolved solution concentrate is being continuously pumped out of the recirculating loop and sent to a bioreactor or feed vessel 612; At the same time, water 606 is being continuously added to the mixing tank 602 to keep the dissolved solution concentrate at a proper volume until all powder is completely dissolved. The dissolved solution concentrate passes through sterilization grade filter 608 to sterilize the dissolved solution concentrate.

FIG. 6B illustrates an end phase of solution preparation. At the end of solution preparation, all powder is completely dissolved, the bulk of the solution in the mixing tank is sent to the bioreactor, and the residual solution is diluted with water 606 in the mixing tank 602 to a point essentially only water with trace amount of components left in the mixing tank 602. The solution reaches its target concentration in the bioreactor or its feed vessel 612.

Mobile Clean-In-Place Skid

A CIP skid may have an onboard neutralization tank with a low-maintenance solid-state pH sensor and can neutralize the used cleaning reagents and safely discharge them to drain, eliminating central neutralization system.

Mobile Sterilization Skid

A conventional bioreactor skid has its own steam-in-place (SIP) sub-system (actuated valves and piping) to manage zone-by-zone steam sterilization of the bioreactor vessel and associated auxiliary equipment (gas inlet/outlet filter, liquid inlet/outlet ports, etc.) within its aseptic envelope. The local SIP sub-system also has many steam traps and piping sections to manage the collection and discharging of steam condensate. In some embodiments, a mobile sterilization skid is utilized to take over the zone-by-zone steam sterilization, and perform the sterilization tasks as a service.

A sterilization skid is a workhorse under this arrangement. It sterilizes the bioreactors and other aseptic vessels, i.e., seed, feed, and harvest, etc. In some embodiments, the sterilization skid can sterilize auxiliary equipment, e.g., transfer hose, sampling device, mobile feed cans.

In addition, gas/liquid filters could be pre-sterilized and filter-integrity-test (FIT) ahead of time, further shorten the bioreactor turnaround time and reduce the contamination risk due to faulty filters.

This skid can also make aseptic connections between two equipment, playing a role similar to a sterile tubing welder and is capable of making aseptic connection/disconnection of hose much bigger diameter than a sterile tubing welder could do. It also connects vessels/containers aseptically and inexpensively without using expensive single-use aseptic connectors or pricy valve clusters.

Figure 7:
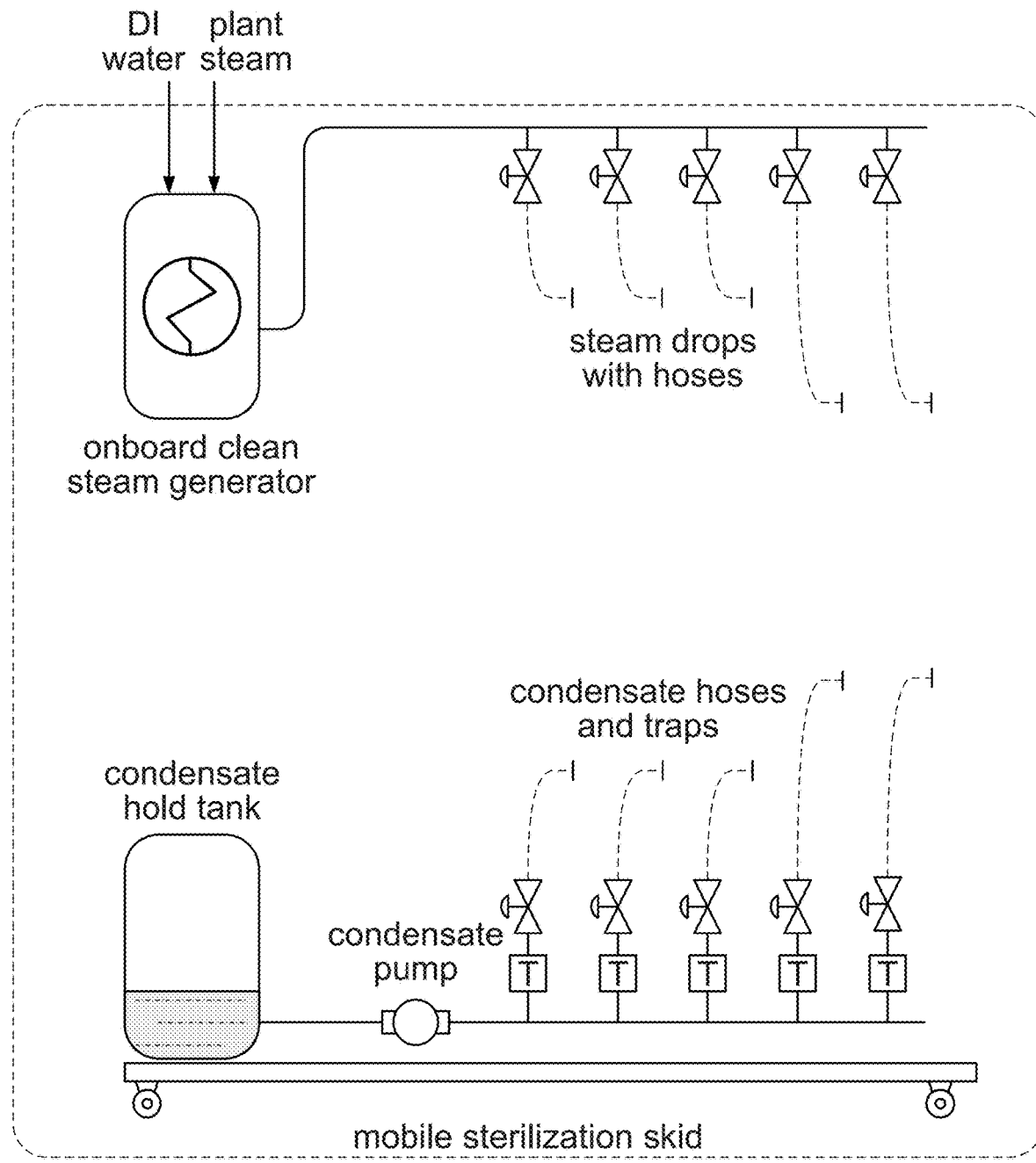
FIG. 7 illustrates a diagram of a mobile sterilization skid in accordance with some embodiments.

FIG. 7 illustrates a diagram of a mobile sterilization skid in accordance with some embodiments. In the example shown, the sterilization steam leverages plant steam as energy source to convert clean water (WFI or RODI grade) into clean steam. The condensate is stored in hold tank temporarily and can be discharged between two services. The sterilization skid has valves to control where steam goes and have steam traps to capture condensate. This skid reduces the complexity of the bioreactor skid.

Figure 8A:
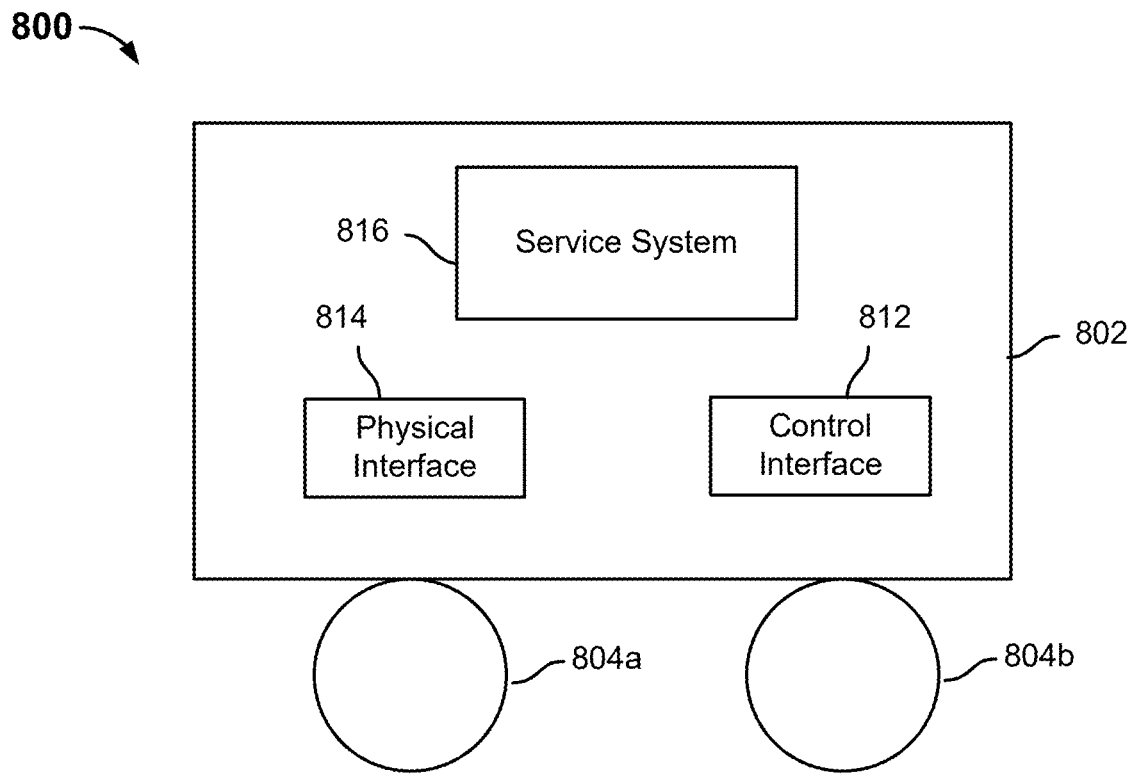
FIG. 8A depicts a block diagram of a mobile bioreactor service system in accordance with some embodiments.

FIG. 8A illustrates a block diagram of a mobile bioreactor service system in accordance with some embodiments. In the example shown, mobile bioreactor service system 800 includes a body 802 and a plurality of wheels 804a, 804b. The body 802 includes a control interface 812 and a physical interface 814. The mobile bioreactor service system 800 may connect to a bioreactor vessel via one or more tubes (e.g., a hose) to physically transfer material to/from the bioreactor vessel. Physical interface 814 may connect the mobile bioreactor service system 800 via one or more tubes. The number of tubes needed to connect the mobile bioreactor service system 800 to the bioreactor vessel depends on the service being performed. For example, the number of tubes needed for a CIP operation may be different than a sterilization operation and/or a solution prep operation. A different mobile bioreactor service system is used for the different operations.

Control interface 812 may include a controller, a microprocessor, a processor, a field programmable gate array, or other type of circuit. Control interface 812 is configured to connect to a skid associated with a bioreactor vessel by wired or wireless protocols. Control interface 812 is configured to connect to one or more valves on the bioreactor vessel and cause them to open and close. Control interface 812 is configured to connect to one or more valves associated with a connector and cause them to open and close. The sequence in which control interface 812 causes one or more valves to open and close depends on the application of the mobile bioreactor service system. For example, the sequence for a CIP operation may be different than a sterilization operation and/or a solution prep operation. Upon being connected to a bioreactor vessel, control interface 812 may automatically control the bioreactor in the manner in which it is programmed to carry out the mobile bioreactor service.

When compared to fixed skids, the complexity associated with connecting mobile bioreactor service system 800 and controlling mobile bioreactor service system 800 is reduced because the interdependencies between the fixed skids and a plurality of bioreactors has been eliminated. For example, utilizing control interface 812 to send a command to open a valve causes a valve associated with a bioreactor connected to mobile bioreactor service system 800 to open. Whereas, in the fixed skid environment, sending a command to open a valve causes a valve associated with a bioreactor to open, however, the consequence of opening the valve associated with the bioreactor needs to be considered before the valve can be opened (e.g., to prevent cross contamination, over pressure, leaking events).

Service system 816 is configured to service a function that is transferred from a bioreactor vessel to mobile bioreactor service system 800. For example, service system 816 may include a system configured perform a CIP operation (e.g., FIG. 11B), a system configured to perform a sterilization operation (e.g., FIG. 12B), or a system configured to perform a solution prep operation (e.g., FIG. 6A).

Figure 8B:
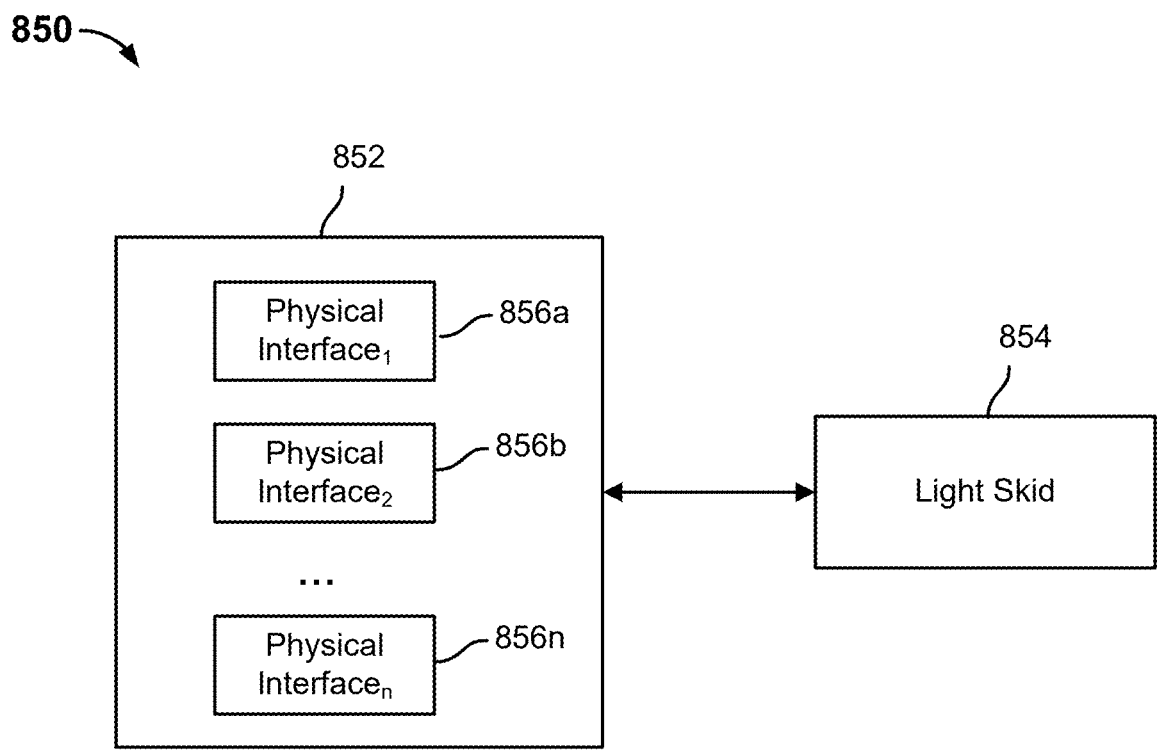
FIG. 8B illustrates a block diagram of a bioreactor in accordance with some embodiments.

FIG. 8B illustrates a block diagram of a bioreactor in accordance with some embodiments. In the example shown, bioreactor 850 includes vessel 852. Vessel 852 is connected to light skid 854 comprised of components needed to sustain live cell culture (i.e., gas flow controllers, sensors, filters, valves at aseptic boundary, and temperature control, etc.). Vessel 852 includes a plurality of physical interfaces 856a, 856b, 856n. Although FIG. 8B depicts vessel 852 having three physical interfaces, vessel 852 may include n physical interfaces. Vessel 852 may include a dedicated physical interface for each mobile bioreactor service system. For example, vessel 852 may include a dedicated physical interface for a mobile CIP system, a dedicated physical interface for a mobile sterilization system, and a dedicated physical interface for a mobile solution prep operation. A physical interface may enable one or more tubes to connect vessel 852 with a mobile bioreactor service system, such as mobile bioreactor service system 800. A physical interface may enable a control interface associated with a mobile bioreactor service system, such as control interface 812, to connect to vessel 852 (e.g., via one or more cables or wireless protocols) and send one or more control signals to control one or more components associated with light skid 854. In some embodiments, bioreactor 852 utilizes a single physical interface and a plurality of different mobile bioreactor service systems are configured to connect the physical interface utilizing a particular connector system (e.g., sterile connector system).

Figure 9:
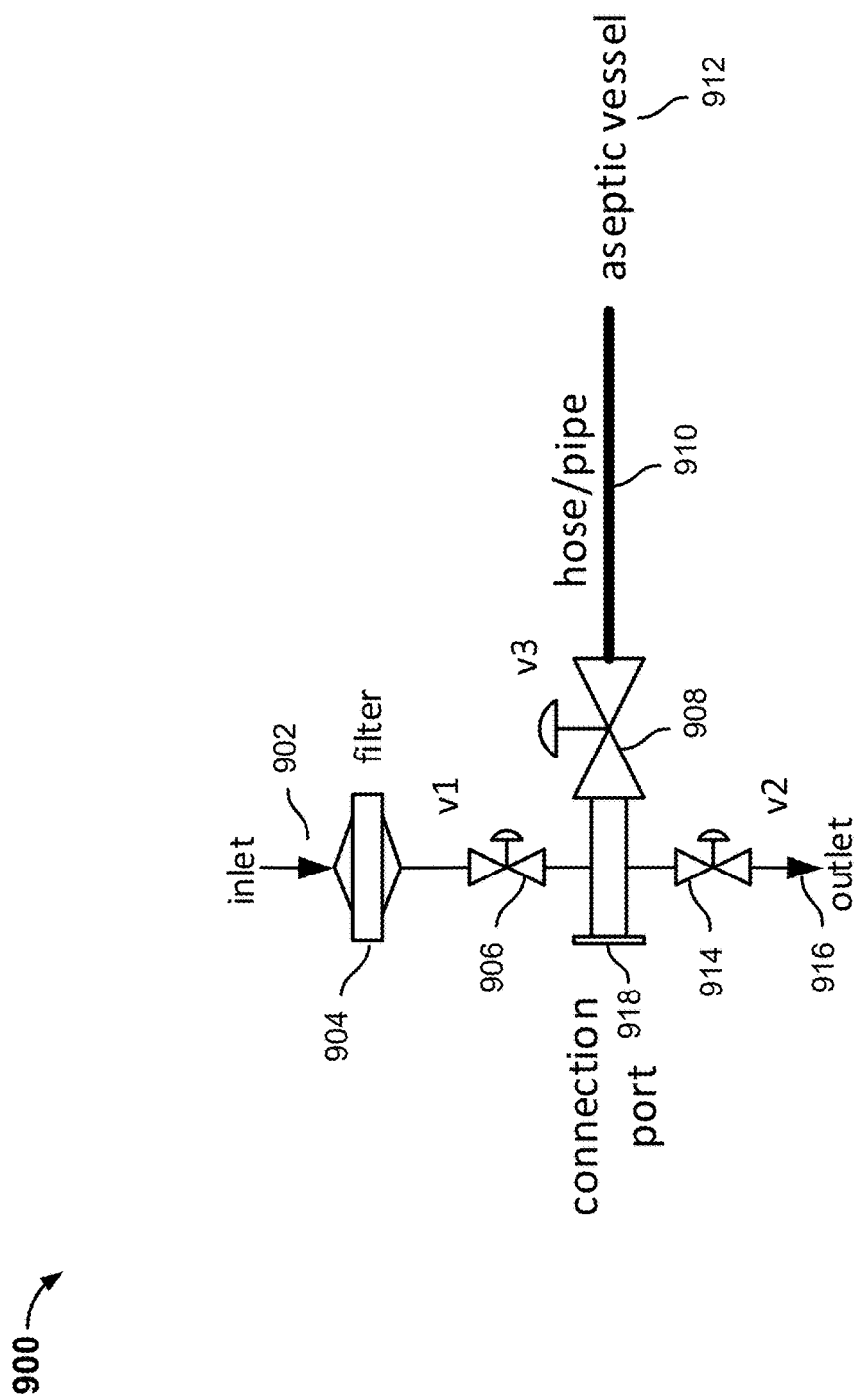
FIG. 9 illustrates a block diagram of a connector system in accordance with some embodiments.

FIG. 9 illustrates a block diagram of a connector system in accordance with some embodiments. In conventional cell culture facilities, aseptic connections are sterilized using steam-in-place method, a process that can take over an hour to establish a sterile connection and an additional half-hour to disconnect a sterile connection. Although single-use connectors and disconnectors offer faster sterile connections, they are costly and have size limitations.

In the example shown, connector system 900 enables quick connection/disconnection between a bioreactor and a mobile media prep skid (or other mobile vessels that supply sterile fluid, e.g., feed, base, antifoam, inoculant, etc. to the bioreactor). Utilizing connector system 900, the connection/disconnect cycle time can be reduced from 1.5 hours to around 15 minutes.

Connector system 900 includes inlet 902. In some embodiments, inlet 902 is steam. The purpose of steam here is to moisturize the interior surface to ensure the thorough killing of bacteria spores. In some embodiments, inlet 902 is chlorine dioxide and air.

Connector system 900 includes filter 904. In some embodiments, filter 904 is a 0.1 μm filter. Connection port 918 may be a tri-clamp connection port that is coupled to valves 906, 908, 914. Valve 908 is a shut-off valve. Valve 906 allows gases, such as chlorine dioxide to enter the tri-clamp connection port and valve 916 allows the gases to exit the tri-clamp connection port via outlet 916. In some embodiments, valves 906, 908, 914 are diaphragm or global valves. In some embodiments, valves 906, 908, 914 share the same valve body.

Hose/pipe 910 is configured to connect to an aseptic vessel 912, such as a seed bioreactor, a feed, or a harvest vessel. In some embodiments, aseptic vessel 912 is a mobile prep skid with a sterilization-grade filter.

Figure 10A:
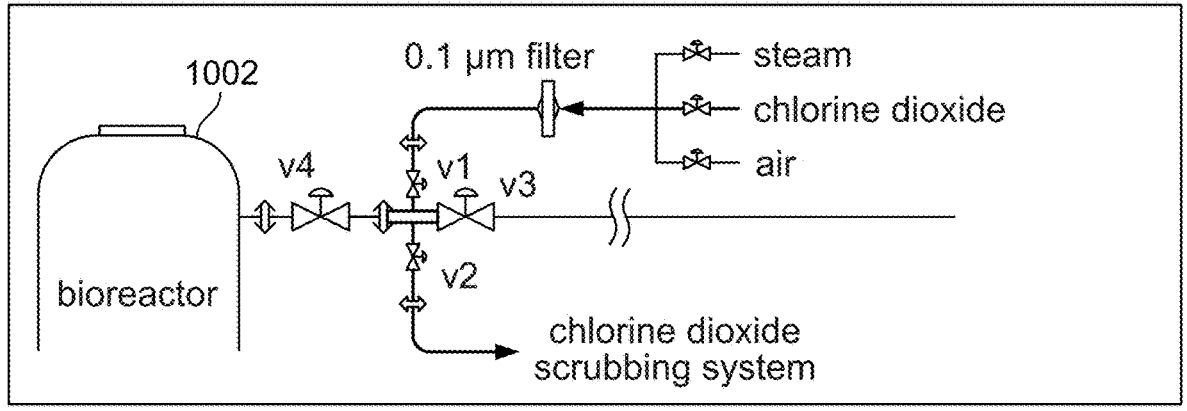
FIGS. 10A-10C illustrate an operation associated with a connection system in accordance with some embodiments.
Figure 10B:
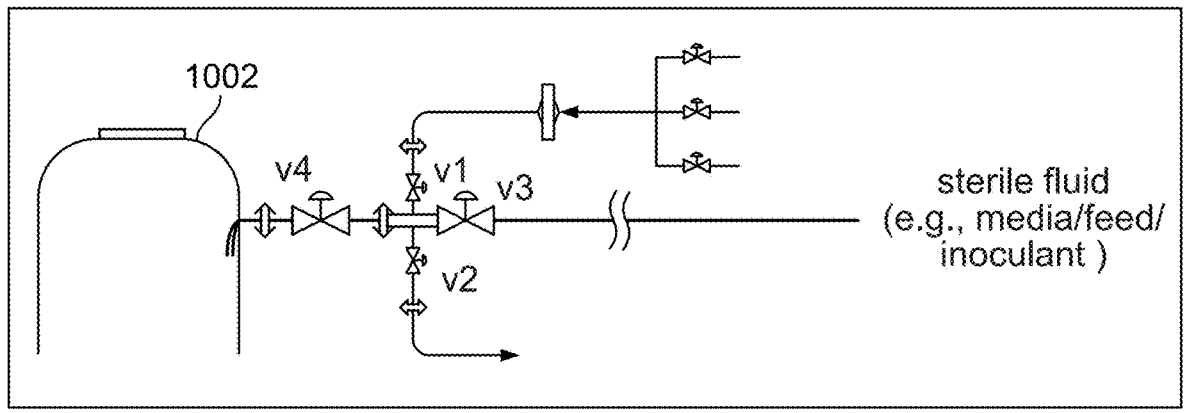
Figure 10C:
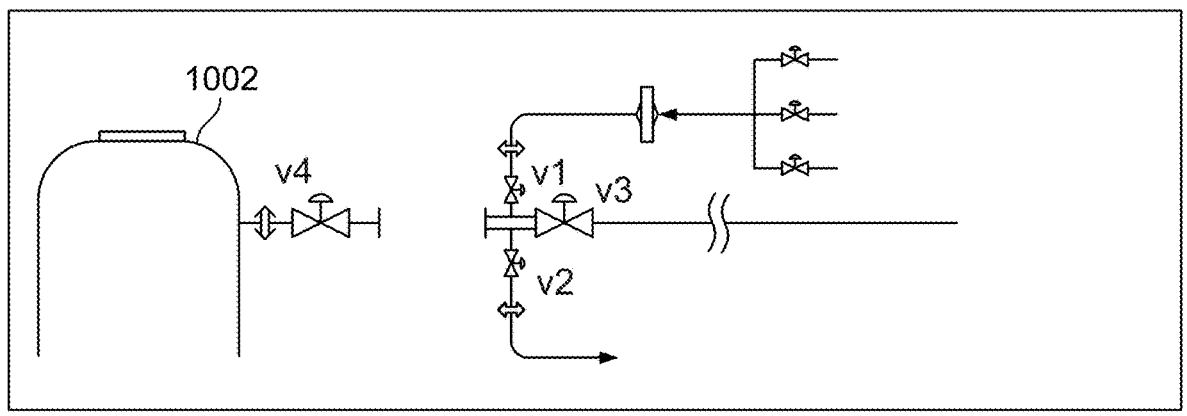

FIGS. 10A-10C illustrate an operation associated with a connection system in accordance with some embodiments. A bioreactor 1002 has been cleaned using a mobile CIP skid and pre-sterilized with a SIP skid. The sterile connector system (e.g., connector system 900) on a mobile media prep skid or a mobile feed vessel enables the sterile transfer of media or feed to bioreactor 1002. In some embodiments, the sterile connector system enables the sterile transfer of cell culture from bioreactor 1002 to a harvest vessel.

In FIG. 10A, valves v3 and v4 are closed. Valves v1 and v2 are open. Steam is first used to moisturize the passage between v3 and v4 (e.g., 1-2 minutes), followed by chlorine dioxide gas for sterilization (e.g., approximately 10 minutes exposure), and finally sterile filtered air to remove any residual chlorine dioxide gas (e.g., approximately 2-3 minutes).

In FIG. 10B, v1 and v2 are closed, and v3 and v4 are open. Sterile fluid (e.g., media/feed/inoculant) is transferred from the mobile media prep skid or mobile feed vessel to bioreactor 1002.

In FIG. 10C, v3 and v4 are closed. Chlorine dioxide gas and air are used to sterilize and clear any residual fluid. In this step, no steam pre-moisturization is needed since the flow path is still wet after fluid transfer. The sterile connector can then be detached from the bioreactor and moved to another bioreactor.

Figure 11A:
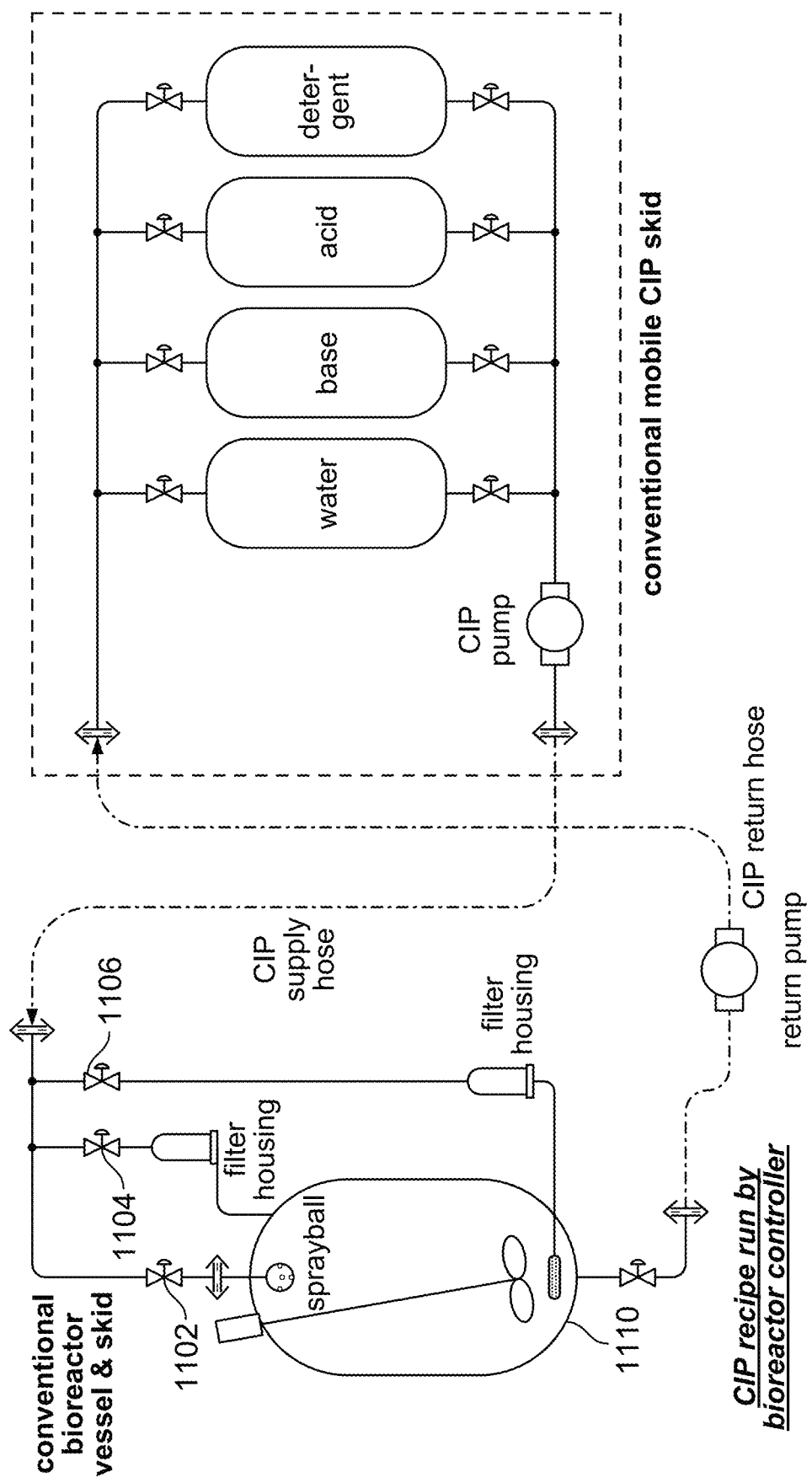
FIG. 11A illustrates a diagram of a conventional mobile CIP skid.

FIG. 11A illustrates a diagram of a conventional mobile stationary CIP skid. Conventional stationary CIP skids have been used in lab-scale or pilot-scale cell culture operations. They pump water and cleaning agents to the bioreactor skid and accept the CIP return at the request of the bioreactor controller, which runs the CIP receipt.

Figure 11B:
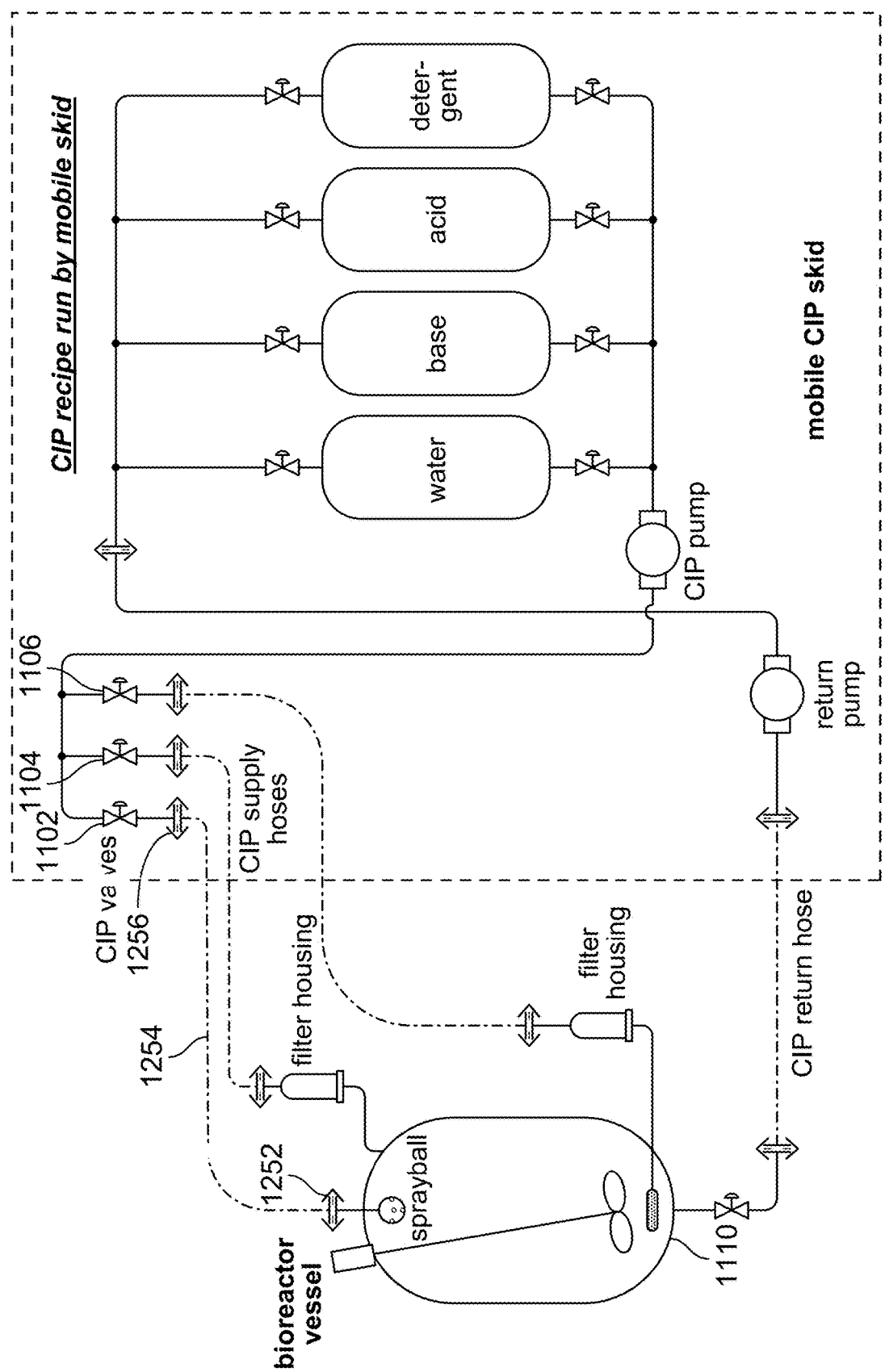
FIG. 11B illustrates a diagram of a mobile CIP skid in accordance with some embodiments.

FIG. 11B illustrates a diagram of a mobile CIP skid in accordance with some embodiments. In contrast to the conventional stationary CIP skid, the mobile CIP skid integrates most of the CIP-related control valves (e.g., valves 1102, 1104, 1106) and runs the CIP recipe. In this embodiment, the bioreactor 1110 does not need a CIP-related control system (e.g., software, instrumentation, valves, etc.) When open, valve 1102 is configured to provide water, base, acid, or detergent to bioreactor vessel 1110 via port 1252 and port 1256, which are connected via hose 1254. Ports 1252, 1256 may be a tri-clamp port or other type of port. Similarly, valve 1104 and 1106 are configured to provide water, base, acid, or detergent to through auxiliary flow paths to the bioreactor vessel 1110 via corresponding ports and hose.

Figure 12A:
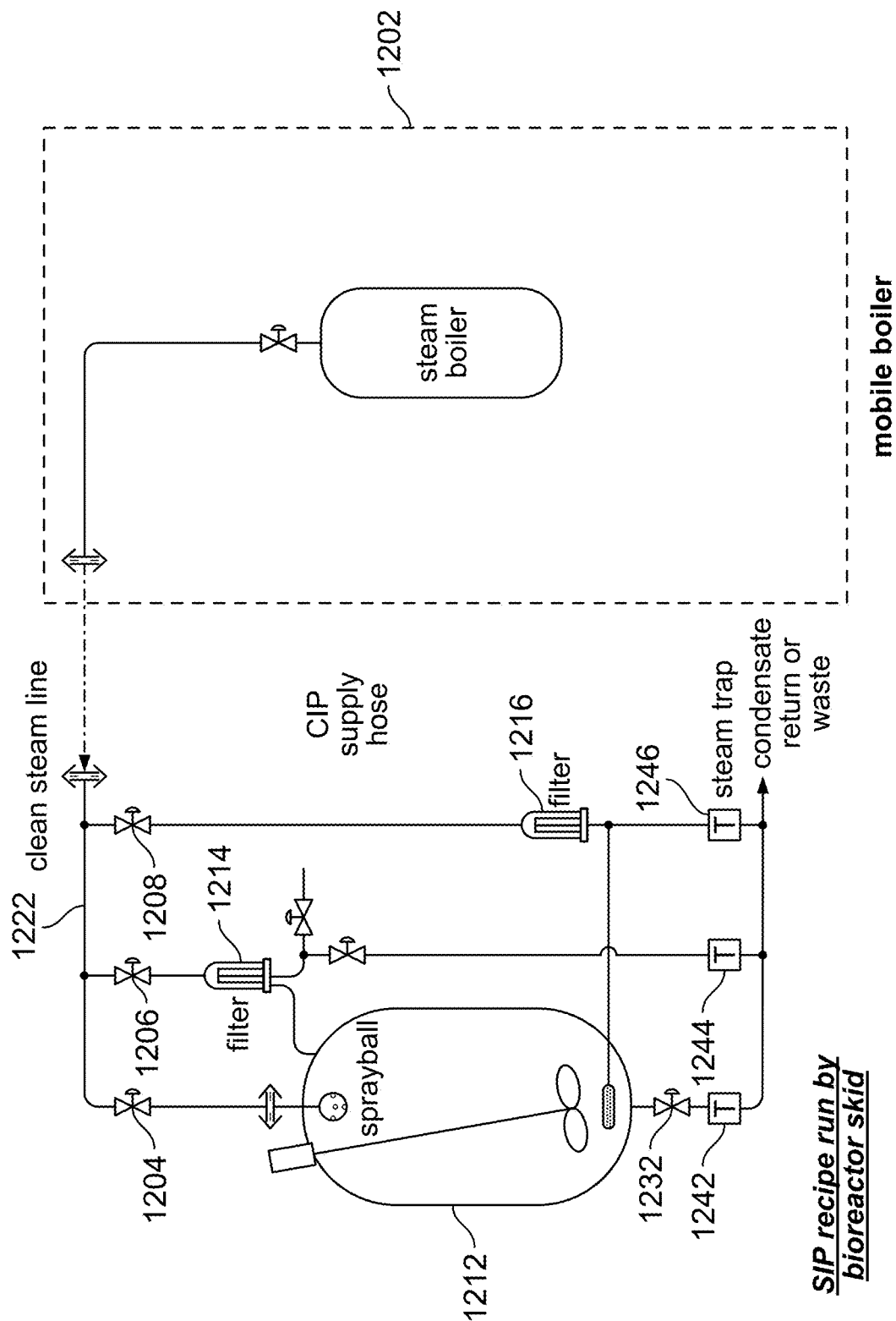
FIG. 12A illustrates a diagram of a bioreactor connected to a conventional mobile boiler.

FIG. 12A illustrates a diagram of a conventional bioreactor connected to a mobile boiler. In the example shown, the mobile boiler 1202 is configured to provide steam to bioreactor 1212 via a clean steam line 1222. The state (e.g., open or closed) of valves 1204, 1206, 1208 determines whether the steam is provided to bioreactor 1212, filter 1214, or filter 1216. Bioreactor 1212 is associated with a skid (not shown) that is configured to execute an SIP recipe.

Figure 12B:
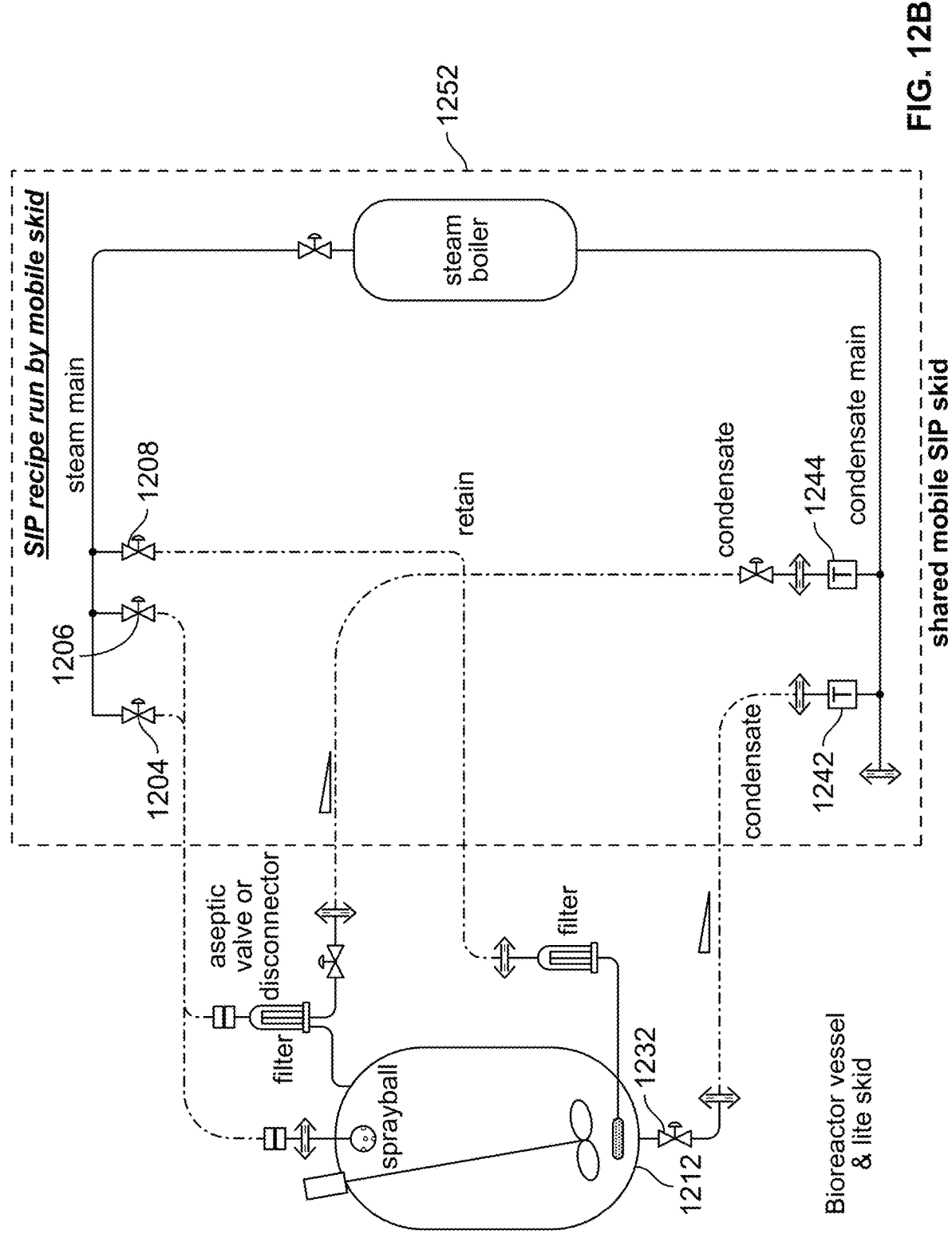
FIG. 12B illustrates a diagram of a bioreactor connected to a mobile SIP skid in accordance with some embodiments.

FIG. 12B illustrates a diagram of a bioreactor connected to a mobile SIP skid in accordance with some embodiments. In the example shown, mobile SIP skid 1252 integrates most of the SIP-related control valve/steam traps (e.g., valves 1204, 1206, 1208; steam traps 1242, 1244) shown in FIG. 12A. The mobile SIP skid 1252 is configured to execute the SIP recipe. In this example, bioreactor 1212 does not need an SIP-related system (software, instrumentation, steam traps, and control valves).

Figure 2A:
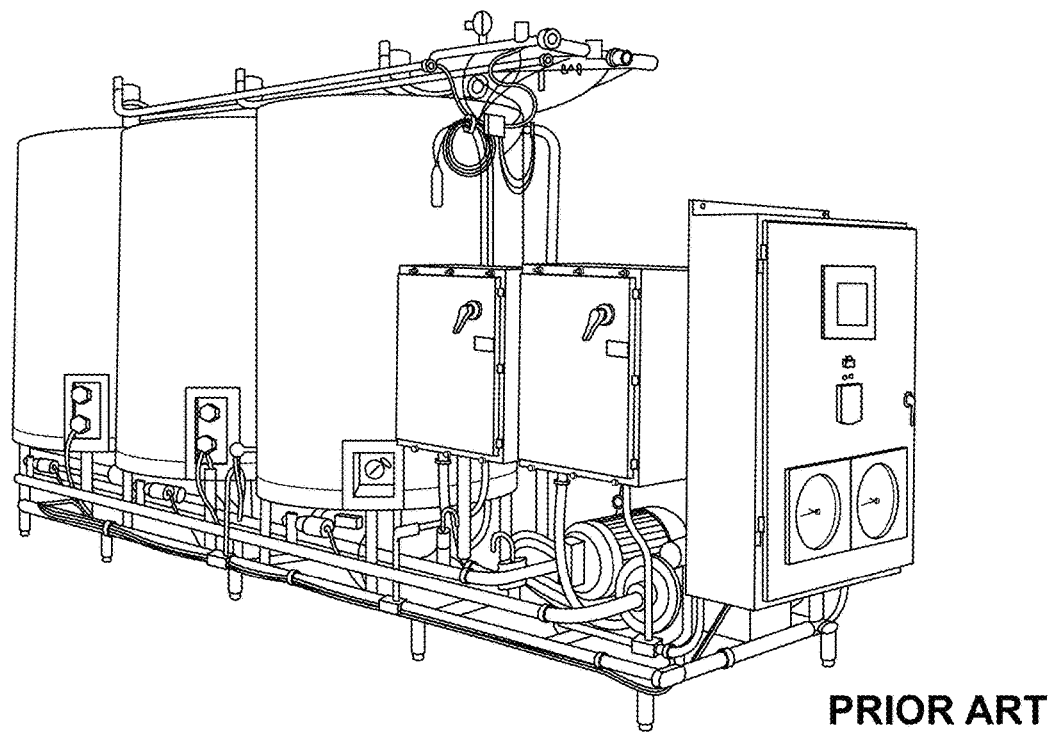
FIG. 2A illustrates an example of a clean-in-place system.
Figure 2B:
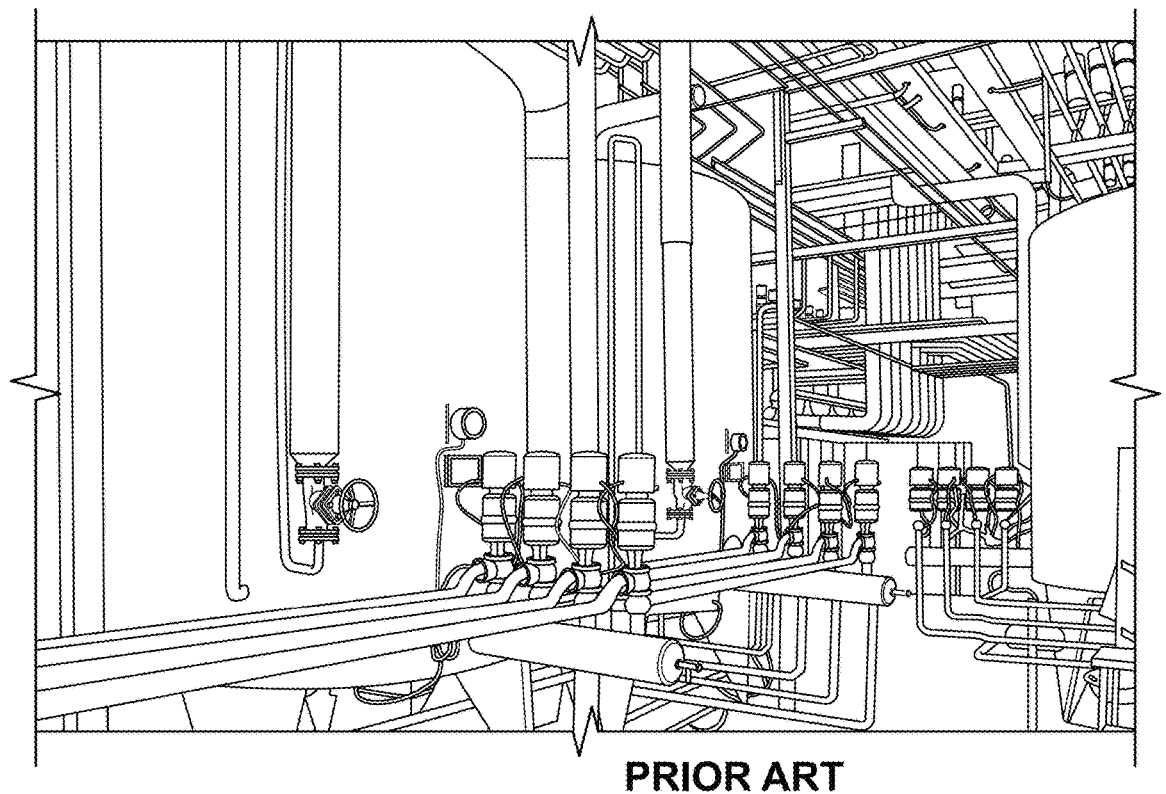
FIG. 2B illustrates an example of a piping network.
Figure 12C:
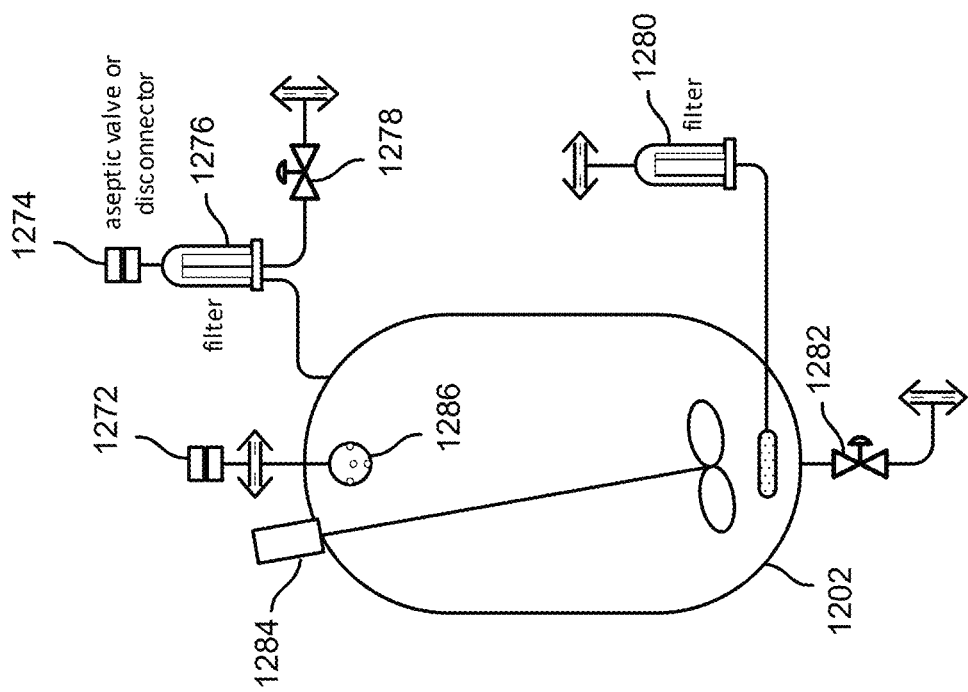
FIG. 12C illustrates a diagram of a bioreactor and a light skid in accordance with some embodiments.

FIG. 12C illustrates a diagram of a bioreactor and a light skid in accordance with some embodiments. After cleaned and sterilized by the mobile CIP and SIP skids, bioreactor 1212 is ready for cell culture. Because bioreactor 1212 passively accepts CIP and SIP services, it does not need complex and expensive systems, such as the systems depicted in FIG. 2A and FIG. 2B, to manage those services. What remains is bioreactor 1212 plus a light skid that includes at least aseptic valves/disconnectors 1272, 1274, filters 1276, 1280, valves 1278, 1282, agitator 1284, and sprayball 1286. The light skid associated with the bioreactor may include one or more other components not shown in FIG. 12C, such as a control system.

Figure 13A:
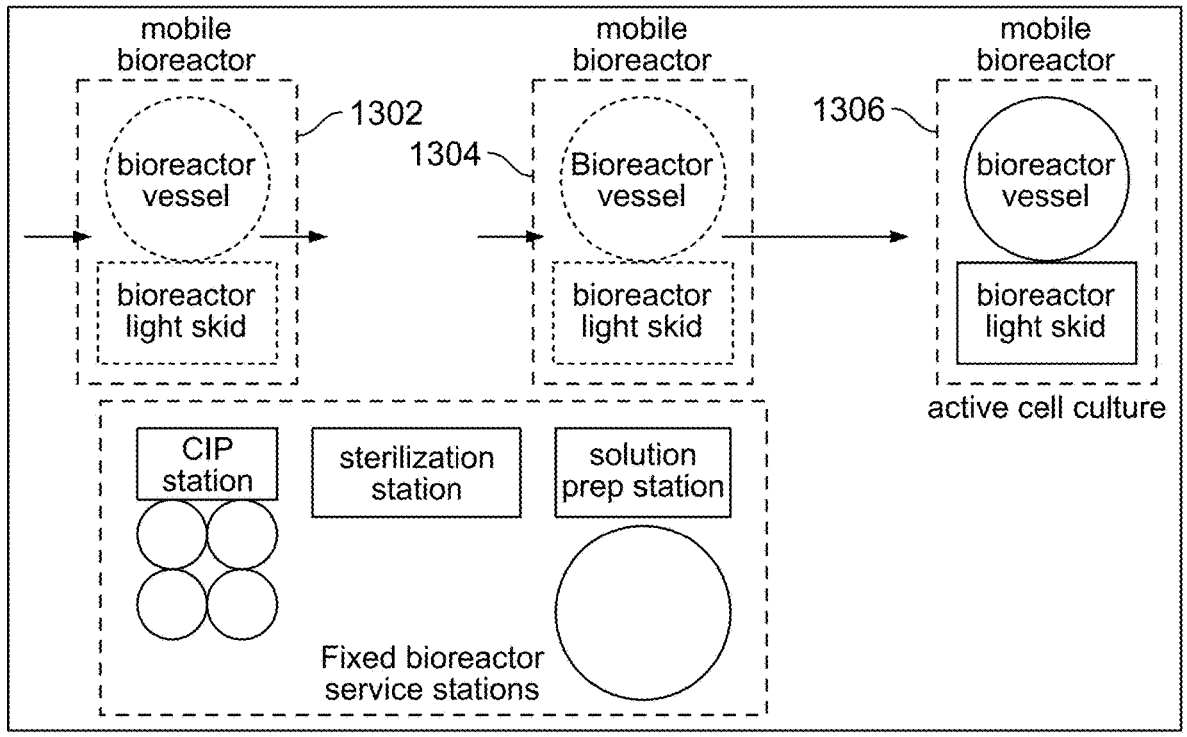
FIG. 13A illustrates a mobile bioreactor with fixed service stations in accordance with some embodiments.

FIG. 13A illustrates a mobile bioreactor with fixed service stations in accordance with some embodiments. In the example shown, the mobile bioreactor moves along a plurality of positions, such as position 1302, position 1304, and position 1306. The mobile bioreactor includes a light skid. The light skid includes the components necessary for the mobile reactor to perform a particular function, such as cultivate cells. The light skid may include a frame, pumps to transfer fluid (e.g., water, chemicals, or other liquids), valves and piping to control the flow of fluids or gases, instruments and sensors (e.g., pressure gauges, flow meters, temperature sensors, etc.), electrical and control systems, filters and strainers, heat exchangers. The mobile bioreactor is mounted on a mobile platform (e.g., on wheels, on track, fork-lifted, jack lifted, etc.). The mobile bioreactor is configured to connect to a stationary service station, such as a stationary CIP station, a stationary sterilization station, a stationary solution prep station, etc., via a connection system, such as connection system 900. There is no need for complex CIP/SIP circuits either in this embodiment.

Figure 13B:
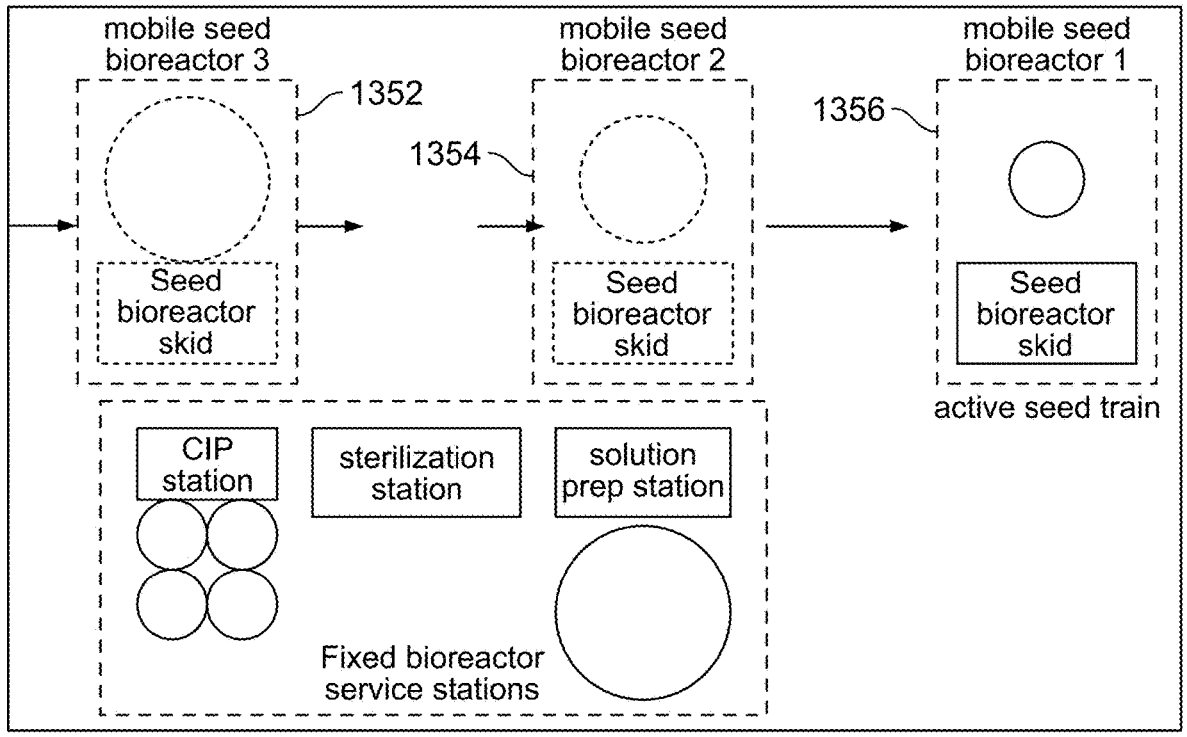
FIG. 13B illustrates a mobile seed bioreactor with fixed service stations in accordance with some embodiments.

FIG. 13B illustrates a mobile seed bioreactor with fixed service stations in accordance with some embodiments. Similar to FIG. 13, the mobile seed bioreactor moves along a plurality of positions, such as position 1352, position 1354, and position 1356. The mobile seed bioreactor includes a light skid. The light skid includes the components necessary for the mobile seed reactor to perform a particular function, such as cultivate cells to expand seed train. The light skid may include a frame, pumps to transfer fluid (e.g., water, chemicals, or other liquids), valves and piping to control the flow of fluids or gases, instruments and sensors (e.g., pressure gauges, flow meters, temperature sensors, etc.), electrical and control systems, filters and strainers, heat exchangers. The mobile seed bioreactor is mounted on a mobile platform (e.g., on wheels, on track, fork-lifted, jack lifted, etc.). The mobile seed bioreactor is configured to connect to a stationary service station, such as a stationary CIP station, a stationary sterilization station, a stationary solution prep station, etc., via a connection system, such as connection system 900.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A mobile bioreactor service system, comprising:
   a control interface that connects to one or more valves;
   a physical interface that connects one or more tubes to a bioreactor enabling process fluids to be physically transferred to/from the bioreactor based on a corresponding state of the one or more valves; and
   a service system that performs a service on the bioreactor, wherein the mobile bioreactor service system is configured to travel along a set of rails to perform the service on the bioreactor and one or more other bioreactors.

2. The mobile bioreactor service system of claim 1, wherein the service is a clean-in-place operation.

3. The mobile bioreactor service system of claim 1, wherein the service is a sterilization operation.

4. The mobile bioreactor service system of claim 1, wherein the service is a solution preparation operation.

5. The mobile bioreactor service system of claim 4, wherein the solution preparation operation includes partially dissolving powder in a mixing tank associated with the mobile bioreactor service system that includes water into a dissolved solution concentrate and recirculating the dissolved solution concentrate from the mixing tank associated with the mobile bioreactor service system to a tangential flow filter associated with the mobile bioreactor service system and back to the mixing tank associated with the mobile bioreactor service system.

6. The mobile bioreactor service system of claim 5, wherein a portion of the dissolved solution concentrate is pumped out from the tangential flow filter to the bioreactor and stored in the bioreactor.

7. The mobile bioreactor service system of claim 6, wherein the water is added to the mixing tank until the portion of the dissolved solution concentrate stored in the bioreactor is at a particular concentration.

8. The mobile bioreactor service system of claim 1, wherein the control interface provides control signals that controls the corresponding state of the one or more valves.

9. The mobile bioreactor service system of claim 1, wherein the process fluids include water, a base, an acid, detergent, steam, chlorine dioxide, air, media, feed, antifoam or an inoculant.

10. The mobile bioreactor service system of claim 1, wherein the mobile bioreactor service system includes a plurality of wheels.

11. The mobile bioreactor service system of claim 1, wherein the mobile bioreactor service system is remotely controlled by a user to travel and service a plurality of bioreactors in a facility, wherein the plurality of bioreactors includes the bioreactor.

12. The mobile bioreactor service system of claim 1, wherein the mobile bioreactor service system is configured to autonomously travel in a facility that includes a plurality of bioreactors, wherein the plurality of bioreactors includes the bioreactor.

13. The mobile bioreactor service system of claim 1, wherein the physical interface includes a sterile connection.

14. The mobile bioreactor service system of claim 13, wherein the sterile connection includes an inlet valve, a shut-off valve, and an outlet valve.

15. The mobile bioreactor service system of claim 14, wherein the inlet valve is configured to provide chlorine dioxide to a connection port that connects the sterile connection to the bioreactor.

16. The mobile bioreactor service system of claim 14, wherein the shut-off valve is connected to an aseptic vessel via a conduit.

17. The mobile bioreactor service system of claim 16, wherein the aseptic vessel is a seed bioreactor.

18. The mobile bioreactor service system of claim 16, wherein the aseptic vessel is a harvest vessel or a feed.

19. A mobile bioreactor service system, comprising:
a control interface that connects to one or more valves;
a physical interface that connects one or more tubes to a bioreactor enabling process fluids to be physically transferred to/from the bioreactor based on a corresponding state of the one or more valves, wherein the physical interface includes a sterile connection, wherein the sterile connection includes an inlet valve, a shut-off valve, and an outlet valve, wherein the inlet valve is configured to provide chlorine dioxide to a connection port that connects the sterile connection to the bioreactor, wherein the shut-off valve is connected to an aseptic vessel via a conduit, wherein the aseptic vessel is a mobile preparation skid; and
a service system that performs a service on the bioreactor.

20. The mobile bioreactor service system of claim 19, wherein the control interface provides control signals that controls the corresponding state of the one or more valves.

21. The mobile bioreactor service system of claim 19, wherein the mobile bioreactor service system includes a plurality of wheels.

22. The mobile bioreactor service system of claim 19, wherein the mobile bioreactor service system is remotely controlled by a user to travel and service a plurality of bioreactors in a facility, wherein the plurality of bioreactors includes the bioreactor.

23. The mobile bioreactor service system of claim 19, wherein the mobile bioreactor service system is configured to autonomously travel in a facility that includes a plurality of bioreactors, wherein the plurality of bioreactors includes the bioreactor.

24. The mobile bioreactor service system of claim 19, wherein the service is a solution preparation operation.

25. The mobile bioreactor service system of claim 24, wherein the solution preparation operation includes partially dissolving powder in a mixing tank associated with the mobile bioreactor service system that includes water into a dissolved solution concentrate and recirculating the dissolved solution concentrate from the mixing tank associated with the mobile bioreactor service system to a tangential flow filter associated with the mobile bioreactor service system and back to the mixing tank associated with the mobile bioreactor service system.

26. The mobile bioreactor service system of claim 25, wherein a portion of the dissolved solution concentrate is pumped out from the tangential flow filter to the bioreactor and stored in the bioreactor.

27. The mobile bioreactor service system of claim 26, wherein the water is added to the mixing tank until the portion of the dissolved solution concentrate stored in the bioreactor is at a particular concentration.

\* \* \* \* \*